United States Patent [19]

Mongelli et al.

[11] Patent Number: 4,514,396
[45] Date of Patent: Apr. 30, 1985

[54] 15-CYCLOALIPHATIC DERIVATIVES OF 13,14-DIDEHYDRO-CARBOPROSTACYCLINS AND PROCESS FOR THEIR PREPARATION

[75] Inventors: Nicola Mongelli; Carmelo Gandolfi, both of Milan, Italy

[73] Assignee: Farmitalia Carlo Erba S.p.A., Milan, Italy

[21] Appl. No.: 536,460

[22] Filed: Sep. 28, 1983

[30] Foreign Application Priority Data

Oct. 1, 1982 [GB] United Kingdom ............... 8228143

[51] Int. Cl.$^3$ .................. C07C 177/00; A61K 31/557
[52] U.S. Cl. ..................................... 514/222; 544/171; 546/206; 560/116; 560/117; 562/498; 562/499; 514/236; 514/319; 514/530; 514/573

[58] Field of Search ............... 560/116, 117; 562/498, 562/499; 424/305, 317, 248.55, 267; 544/171; 546/206

[56] References Cited

FOREIGN PATENT DOCUMENTS

| | | | |
|---|---|---|---|
| 38131 | 10/1981 | European Pat. Off. | ............ 560/117 |
| 3209702 | 9/1983 | Fed. Rep. of Germany | ...... 560/116 |
| 2013661 | 8/1979 | United Kingdom | ................ 560/119 |

*Primary Examiner*—Robert Gerstl
*Attorney, Agent, or Firm*—Murray, Whisenhunt and Ferguson

[57] ABSTRACT

13, 14 didehydro-15 cyclic prostacyclins have been prepared.

14 Claims, No Drawings

15-CYCLOALIPHATIC DERIVATIVES OF 13,14-DIDEHYDRO-CARBOPROSTACYCLINS AND PROCESS FOR THEIR PREPARATION

The present invention relates to new 15-cycloaliphatic derivatives of 13,14-didehydro-carboprostacyclins, to a process for their preparation and to pharmaceutical and veterinary compositions containing them.

Prostacyclins are a well known class of compounds having the basic structure of prostacyclin, or $PGI_2$

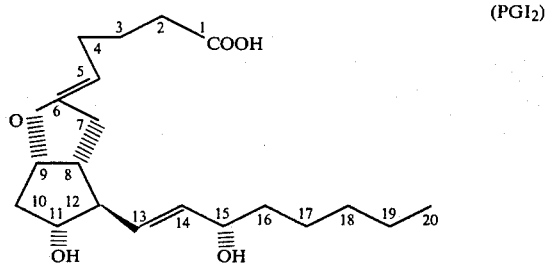

(PGI₂)

Literature referring to prostacyclin includes, for example, Nature, 263, 663, (1976); J. Am. Chem. Soc. 99, 4182 (1977); Prostaglandins 12, 915 (1976); and J. Am. Chem. Soc. 99, 2006 (1977).

Carboprostacyclins are a well known class of compounds too, having a basic structure which differs from the structure of prostacyclin in that the 6,9-epoxy group of $PGI_2$ is replaced by a 6,9-methylene group. Thus, the most representative compound of this class is just carboprostacyclin, or carbo-$PGI_2$

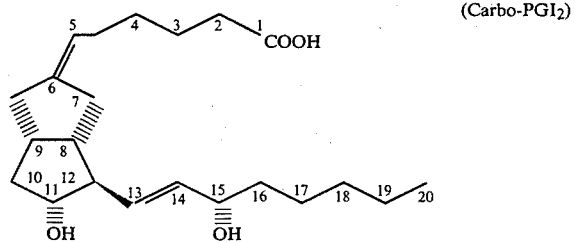

(Carbo-PGI₂)

Literature relating to carboprostacyclin and derivatives thereof includes, for example, UK Pat. No. 2012265B, UK Pat. No. 2014143B, UK Pat. No. 2019847B, UK Pat. No. 2017699B, UK Pat. No. 2013661B and European Pat. No. 11591. In the hereabove cited UK Pat. Nos. 2012265B, 2014143B and 2019847B no description is given of carboprostacyclins carrying a cycloaliphatic group on the bottom chain, or ω-chain, of the carbo-$PGI_2$ structure, i.e. on the chain linked to the 12-position.

U.K. Pat. No. 2017699B describes carboprostacyclin compounds having a cycloalkyl group on said ω-chain, including some wherein the cycloalkyl group is bonded to the 15-position of the carbo-$PGI_2$ structure: however only compounds having a single bond or a trans double bond, between the 13- and the 14-position, but not a triple bond, are described therein. UK Pat. No. 2013661B describes carboprostacyclin derivatives having a cycloaliphatic group on the ω-chain and a triple bond on the 13,14-position but the possibility that the ω-cycloaliphatic group is bonded to the 15-position of the carbo-$PGI_2$ structure is not therein contemlated for cycloaliphatic groups with more than three carbon atoms.

European Pat. No. 11591 describes carboprostacyclin compounds whose general formula involves the presence of a cycloalkyl group at the 15-position of the ω-chain and of a triple bond at the 13,14-position: no specific mention is however made in said European Pat. No. 11591 either of compounds having a cycloalkyl group anywhere on the ω-chain or of compounds having a triple bond at the 13-14-position. The present invention provides just carboprostacyclin compounds characterized by having a cycloaliphatic substituent on the 15-position of the ω-chain and, at the same time, an acetylenic bond, i.e. a triple bond, at the 13,14-position of the carbo-$PGI_2$ structure. More precisely the invention provides optically active or racemic 15-cycloaliphatic derivatives of 13,14-didehydro carboprostacyclins of the following general formula (I)

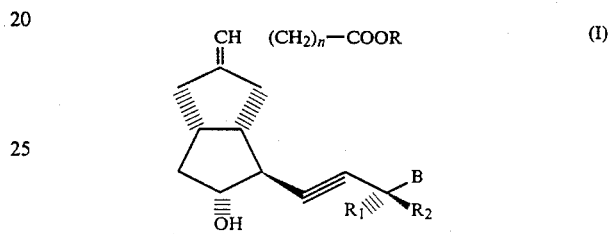

(I)

wherein

R is hydrogen or a $C_1$–$C_6$ alkyl group optionally substituted by a group

wherein each of $R_3$ and $R_4$ is, independently, hydrogen or $C_1$–$C_6$ alkyl, or $R_3$ and $R_4$, taken together with the nitrogen atom to which they are linked, form a pentatomic or hexatomic heteromonocyclic ring optionally containing a further heteroatom chosen from O and S; n is zero or an integer of 1 to 5;

one of $R_1$ and $R_2$ is hydrogen or $C_1$–$C_6$ alkyl and the other is hydroxy; and B represents: (a) a $C_4$–$C_7$ monocycloaliphatic group either unsubstituted or substituted by one or more substituents chosen from $C_1$–$C_6$ alkyl, $C_2$–$C_6$ alkenyl and $C_1$–$C_6$ alkylidene; (b) norbornyl; or (c) adamantyl, and the pharmaceutically or veterinarily acceptable salts of the compounds of formula (I).

The invention also includes the pharmaceutical and veterinary compositions containing a suitable carrier and/or diluent and, as an active principle, a compound of formula (I) or a pharmaceutically or veterinarily acceptable salt thereof. All the possible isomers of formula (I), both stereoisomers, e.g. cis (or Z) and trans (or E) isomers, and optical isomers, i.e. enantiomers, and diastereoisomers, and their mixtures, and the metabolites and the metabolic precursors or bioprecursors of the compounds of formula (I) are included in the scope of the invention. In this application, a dashed line ("''') refers to a ring substituent in the α-configuration, that is, below the plane of the ring, to a bicyclo octane substituent in the endo configuration, and to a side chain substituent in the α-configuration. A wedged line ( ), on the other hand, refers to a ring substituent in the β-configuration, that is above the plane of the ring, to a bicyclo octane substituent in the exo-configuration, and to a side chain substituent in the β-configuration. Furthermore, the absolute "R" or "S" configurations of the chiral centers are assigned according to the sequence-rule procedure of JUPAC for the Nomenclature of Organic Chemistry (J.O.C. 35. 9 2849, 1970). Where unspecified "R,S" mixtures are intended.

In the compounds of this invention, there are 2 possible geometric isomers arising from the configuration of the double bond exocyclic to the bicyclo octane ring depending on whether the chain linked to this double bond (chain α) is on the same side as or the opposite side from the chain (chain ω) linked to the 12-position on the bicyclo octane ring: in the first case, the exocyclic double bond is defined as Z, i.e. cis; in the second, it is E, i.e. trans. The symbol ~ in formula (I) means that both geometric isomers are covered by this invention, both separately and in mixtures.

Furthermore each Z or E or Z,E compound may be a racemate (±) or an optically active compound, i.e. a (+) or (−) enantiomer. Pharmaceutically or veterinarily acceptable salts of the compounds of formula (I) include both the salts of the compounds of formual (I) wherein R is hydrogen with a pharmaceutically or veterinarily acceptable inorganic or organic base, and the salts of the compounds of formula (I) wherein R is an alkyl group substituted by a

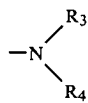

group with a pharmaceutically or veterinarily acceptable inorganic acid. Acceptable inorganic bases may be, for example, the hydroxides of alkali, e.g. sodium or potassium, or alkaline earth, e.g. calcium or magnesium, metals, zinc and aluminum. Acceptable organic bases may be, for example, amines like methylamine, diethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and other similar aliphatic, aromatic and heterocyclic amines like piperidine, morpholine, pyrrolidine, piperazine, as well as substituted derivatives like 1-methylpiperidine, 4-ethylmorpholine, 1-isopropylpyrrolidine, 2-methylpyrrolidine, 1,4-dimethylpiperazine, 2-methylpiperidine, hydrophilic derivatives like mono-, di- and triethanolamine, 2-amino-2-butanol, 2-amino-1-butanol, 2-amino-2-ethyl-1,3-propanediol, 2-amino-2-methyl-1-propanol, tris-(hydroxymethyl)-aminomethane, N-phenylethanolamine, N-(p-tert-amylphenyl)-diethanolamine, ephedrine, procain, and α and β amino acids like lysine and arginine. Pharmaceutically or veterinarily acceptable inorganic acids include, for example, hydrochloric, hydrobromic, nitric, sulfuric; while organic acids include, for example, citric, fumaric, tartaric, malic, maleic, methanesulfonic and ethanesulfonic.

The alkyl, alkenyl and alkylidene groups may be branched or straight chain groups.

A $C_1$–$C_6$ alkyl group is, preferably, a $C_1$–$C_4$ alkyl group, in particular methyl, ethyl or tert-butyl.

A $C_2$–$C_6$ alkenyl group is, preferably, a $C_2$–$C_4$ alkenyl group, in particular vinyl or allyl.

A $C_1$–$C_6$ alkylidene group is, preferably, a $C_1$–$C_4$ alkylidene group, in particular methylene (i.e. $=CH_2$) or isopropylidene (i.e.

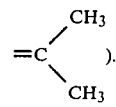

).

A group

wherein $R_3$ and $R_4$ are, independently, hydrogen or $C_1$–$C_6$ alkyl is preferably, amino, methylamino, dimethylamino or diethylamino.

A group

wherein $R_3$ and $R_4$ taken together with the nitrogen atom to which they are linked form a heteromonocyclic ring as defined above, is, preferably, a hexatomic or pentatomic heteromonocyclic ring optionally containing oxygen or sulphur, preferably oxygen, as additional heteroatom.

Examples of hexatomic rings are piperidino, morpholino and thiomorpholino; an example of pentatomic ring is pyrrolidino. Preferred rings are the hexatomic rings, in particular piperidino and morpholino.

When in the above formula (I) R is an unsubstituted $C_1$–$C_6$ alkyl group it is, preferably, methyl or ethyl, most preferably methyl.

When R is a $C_1$–$C_6$ alkyl group substituted by

it is, preferably a $C_1$–$C_3$ alkyl group, in particular ethyl, substituted by a group

which is preferably chosen from amino, methylamino, dimethylamino, diethylamino, piperidino, morpholino or thiomorpholino.

Preferred R groups are hydrogen, methyl, β-diethylaminoethyl, β-piperidinoethyl and β-morpholinoethyl.

When B is a $C_4$–$C_7$ monocycloaliphatic group it may be either a saturated or a unsaturated monocycloaliphatic group optionally substituted as reported above.

Examples of saturated monocycloaliphatic groups are cycloalkyl groups like cyclobutyl, cyclopentyl and cyclohexyl; examples of unsaturated cycloaliphatic groups are cycloalkenyl groups like cyclohexenyl and cyclopentenyl. When B is norbornyl it is, preferably, 7-norbornyl. Preferably B is a $C_4$-$C_7$ monocycloalkyl group and, more preferably, a cyclopentyl or cyclohexyl group, either unsubstituted or substituted by a substituent chosen from $C_1$-$C_4$ alkyl, in particular methyl, ethyl or tert.butyl; $C_2$-$C_4$ alkenyl, in particular vinyl or allyl; and $C_1$-$C_4$ alkylidene, in particular methylene or isopropylidene. Most preferred group B is cyclopentyl either unsubstituted or substituted as reported hereabove. Preferably one of $R_1$ and $R_2$ is hydrogen and the other is hydroxy. Preferably n is 3 or 4. Preferred salts are the salts of the compounds of formula (I) wherein R is hydrogen with a pharmaceutically or veterinarily acceptable base, e.g. one of the bases listed above.

A preferred class of compounds under this invention is represented by the compounds of formula (I) wherein R is hydrogen, $C_1$-$C_6$ alkyl, $\beta$-piperidino-$C_1$-$C_3$ alkyl or $\beta$-morpholino-$C_1$-$C_3$ alkyl; n is 3 or 4; one of $R_1$ and $R_2$ is hydrogen and the other is hydroxy; and B is cyclopentyl or cyclohexyl, either unsubstituted or substituted by a substituent chosen from $C_1$-$C_4$ alkyl, $C_2$-$C_4$ alkenyl and $C_1$-$C_4$ alkylidene, and the pharmaceutically or veterinarily acceptable salts thereof.

In the above preferred class of compounds with formula (I) B is, most preferably, cyclopentyl either unsubstituted or substituted as therein reported. When in the above preferred class of compounds of the invention R is $C_1$-$C_6$ alkyl, this is, preferably, methyl or ethyl; when R is $\beta$-piperidino-$C_1$-$C_3$ alkyl, it is, preferably, $\beta$-piperidinoethyl; when R is $\beta$-morpholino-$C_1$-$C_3$-alkyl, it is, preferably, $\beta$-morpholinoethyl. When B is cyclopentyl or cyclohexyl substituted by $C_1$-$C_4$ alkyl, the alkyl is, preferably, methyl or ethyl; when B is cyclopentyl or cyclohexyl substituted by $C_2$-$C_4$ alkenyl, the alkenyl is, preferably, vinyl; when B is cyclopentyl or cyclohexyl substituted by $C_1$-$C_4$ alkylidene, the alkylidene is, preferably, isopropylidene.

The nomenclature used to identify the specific compounds falling within the invention is the same illustrated in the above mentioned Pat. No. 2013661B. According to such a nomenclature, relating to the prostacyclanoic acid structure, the compounds of the invention are referred to as 9a-deoxy-9a-methylene-prostacycl-5-en-13-ynoic acid derivatives with the addition that the prefix "5Z" or "5E" or 5(Z,E) is used to identify the configuration of the double bond exocyclic to the bicyclooctane system. When unspecified a racemic compound is intended.

As an example of this nomenclature, the compound of formula (I) wherein R is hydrogen, n is 3, $R_1$ is hydroxy, $R_2$ is hydrogen, B is cyclohexyl and the configuration of the exocyclic double bond carrying the α-chain is "E" is named;

5E-11 α, 15S-dihydroxy-9a-deoxy-9a-methylene-ω-pentanor-15-cyclohexyl-prostacycl-5-en-13-ynoic acid.

Specific examples of preferred compounds under this invention are the following compounds, both in the form of racemates and in the form of (+) enanitomers:

5E-11 α, 15S-dihydroxy-9a-deoxy-9a-methylene-ω-pentanor-15-cyclopentyl-prostacycl-5-en-13-ynoic acid;
5E-11 α, 15S-dihydroxy-9a-deoxy-9a-methylene-ω-pentanor-15-[(3'-methyl)-cyclopentyl]-prostacycl-5-en-13-ynoic acid;
5E-11 α, 15S-dihydroxy-9a-deoxy-9a-methylene-ω-pentanor-15-[(3'-ethyl)-cyclopentyl]-prostacycl-5-en-13-ynoic acid;
5E-11 α, 15S-dihydroxy-9a-deoxy-9a-methylene-ω-pentanor-15-[(3'-isopropylidene)-cyclopentyl]-prostacycl-5-en-13-ynoic acid;
5E-11α, 15S-dihydroxy-9a-deoxy-9-methylene-ω-pentanor-15-cyclohexyl-prostacycl-5-en-13-ynoic acid;
5-E-11α, 15S-dihydroxy-9-a-deoxy-9a-methylene-ω-pentanor-15-[(4'-methyl)-cyclohexyl]-prostacycl-5-en-13-ynoic acid;
5E-11α, 15S-dihydroxy-9a-deoxy-9a-methylene-ω-pentanor-15-[(4'ethyl)-cyclohexyl]-prostacycl-5-en-13-ynoic acid;
5E-11α, 15S-dihydroxy-9a-deoxy-9a-methylene-ω-pentanor-15[(4'-isopropylidene)-cyclohexyl]-prostacycl-5-en-13-ynoic acid;
5Z-11α, 15S-dihydroxy-9A-deoxy-9a-methylene-ω-pentanor-15-cyclopentyl-prostacycl-5-en-13-ynoic acid;
5Z-11 α, 15S-dihydroxy-9a-deoxy-9a-methylene-ωpentanor-15-[(3'-methyl)-cyclopentyl]-prostacyl-5-en-13-ynoic acid;
5Z-11α, 15S-dihydroxy-9a-deoxy-9a-methylene-ω-pentanor-15-[(3'-ethyl)-cyclopentyl]-prostacycl-5-en-13-ynoic acid;
5Z-11α, 15S-dihydroxy-9a-deoxy-9a-methylene-ω-pentanor-15[(30'-isopropylidene)-cyclopentyl]-prostacycl-5-en-13-ynoic acid;
5Z-11α, 15S-dihydroxy-9a-deoxy-9a-methylene-ω-pentanor-15-cyclohexyl-prostacycl-5-en-13-ynoic acid;
5Z-11α,15S-dihydroxy-9a-deoxy-9a-methylene-ω-pentanor-15-[(4'-methyl)-cyclohexyl]-prostacycl-5-en-13-ynoic acid;
5Z-11α,15S-dihydroxy-9a-deoxy-9a-methylene-ω-pentanor-15-[(4'-ethyl)-cyclohexyl-]prostacycl-5en-13-ynoic acid;
5Z-11 α, 15S-dihydroxyl-9a-deoxy-9a-methylene-ω-pentanor-15-[(4'-isopropylidene)-cyclohexyl]-prostacycl-5-en-13-ynoic acid;
5(Z,E)-11α, 15S-dihydroxy-9a-deoxy-9a-methylene-ω-pentanor-15-cyclopentyl-prostacycl-5-en-13-ynoic acid;
5(Z,E)-11α, 15S-dihydroxy-9a-deoxy-9-methylene-ω-pentanor-15[(3'-methyl)-cyclopentyl]-prostacycl-5-en-13-ynoic acid;
5(Z,E)-11α,15S-dihydroxy-9a-deoxy-9a-methylene-ω-pentanor-15-[(3'-ethyl)-cyclopentyl]-prostacycl-5-en-13-ynoic acid;
5(Z,E)-11α, 15S-dihydroxy-9a-deoxy-9a-methylene-ω-pentanor-15-[(3'-isopropylidene)-cyclopentyl]-prostacycl-5-en-13-ynoic acid;
5(Z,E)-11α, 15S-dihydroxy-9a-deoxy-9a-methylene-ω-pentanor-15-cyclohexyl-prostacycl-5-en-13-ynoic acid;
5(Z,E)-11 α,15S-dihydroxy-9a-deoxy-9a-methylene-ω-pentanor-15-[(4'-methyl)-cyclohexyl]-prostacycl-5-en-13-ynoic acid;
5(Z,E)-11α, 15S-dihydroxy-9a-deoxy-9a-methylene-ω-pentanor-15-[(4'-ethyl)-cyclohexyl]-prostacycl-5-en-13-ynoic acid;
5(Z,E)-11α, 15S-dihydroxy-9-a-deoxy-9a-methylene-ω-pentanor-15-[(4'-isopropylidene)-cyclohexyl]-prostacycl-5-en-13-ynoic acid;
and the pharmaceutically or veterinarily acceptable salts thereof and the $C_1$-$C_6$ alkyl-esters, $\beta$-piperidinoethyl-esters and $\beta$-morpholinoethyl-esters thereof.

Among the specific preferred compounds indicated above, the (+) enantiomers are particularly preferred.

The compounds of the invention are prepared by a process comprising reacting a compound of formula (11)

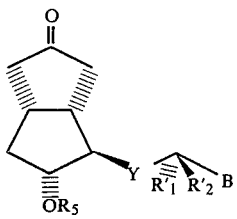

wherein R is as defined above, $R_5$ is hydrogen or a hydroxy protecting group, one of $R'_1$ and $R'_2$ is hydrogen or $C_1$-$C_6$ alkyl and the other is a group —$OR_5$ wherein $R_5$ is as hereabove defined, and Y is —C≡C— or —CH=CZ— wherein Z is chlorine, bromine or iodine, with a Wittig reagent of formula (111)

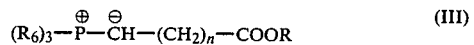

wherein n and R are as defined above and $R_6$ is an aryl or alkyl group, and removing the protecting groups possibly present, and, if desired, esterifying an obtained compound of formula (I) wherein R is hydrogen to give a compound of formula (I) wherein R is $C_1$-$C_6$ alkyl optionally substituted as reported above, or saponifying an obtained compound of formula (I) wherein R is $C_1$-$C_6$ alkyl optionally substituted as reported above to give a compound of formula (I) wherein R is hydrogen, or a salt thereof, and/or, if desired, salifying a compound of formula (I) or obtaining a free compound from a salt, and/or, if desired separating a mixture of isomers of formula (I) into the single isomers. When in the compound of formula (II) Y is —CH=CZ—, the halogen Z is, preferably, bromine.

When in the compound of formula (II) $R_5$ is a hydroxy protecting group it is, for example, an ether or ester residue which may be readily split under mild conditions, for instance by acid hydrolysis. Preferred groups include silyl ether residues: for instance trialkyl-silyl like trimethyl, dimethyl-tert-butyl, dimethyl-isopropyl, or dimethylethylsilyl; and also acetal and enol ether residues: for instance, tetrahydropyranyl, tetrahydrofuranyl, dioxanyl, oxathianyl, or groups such as

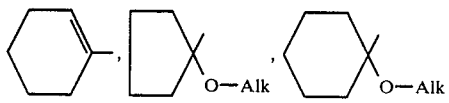

where Alk is $C_1$-$C_6$ alkyl.

When in the compound of formula (III) $R_6$ is aryl it is preferbly, phenyl; when $R_6$ is $C_1$-$C_6$ alkyl ether is preferred. The reaction between a compound of formula (II) and a compound of formula (III) is preferably carried out in the presence of a solvent and, preferably, using an excess of the Wittig reagent of formula (III), e.g. from about 1.5 to about 5 moles of Wittig reagent per 1 mole of the compound of formula (II). The solvent may be any solvent which can, in general, be used for Wittig reactions. Preferably it is an inert organic solvent chosen from ethers, both linear and cyclic, e.g. diethyl ether, tetrahydrofuran, dioxane or dimethoxyethane; aliphatic or aromatic hydrocarbons, e.g. n-hexane, n-heptane, benzene, toluene or xylene; dialkylsulphoxides, e.g. dimethylsulphoxide; aliphatic acid dialkylamides, e.g. dimethylformamide or dimethylacetamide; halogenated hydrocarbons, e.g. dichloromethane or chloroform; and phosphoric acid triamides, hexmethylphosphoramide for example. Dimethylsulphoxide is a particularly preferred solvent. The reaction temperature may range from about −10° C. to the reflux temperature of the solvent used although room temperature is particularly preferred. The reaction is normally carried out in the presence of a base which may be, for example, potassium tert.butoxide or sodium hydride and, preferably, operating under nitrogen atmosphere.

Preferably a compound of formula (II) is used wherein Y is —CH=CZ— wherein Z is as defined above, preferably bromine or iodine, in particular bromine, as, in this instance, both the triple bond formation and the alkylation with the Wittig reagent take place at the same time in an only one step. In this case it is preferred to use not less than about two moles of compound (III) per mole of compound (II). A greater excess of the Wittig reagent, up to 5 moles per mole of compound (II), may be, however, employed and in this way the reaction times can be considerably reduced. The time required by the reaction may vary, depending upon the used reaction conditions, within the range from 0.5 to 24 hours. The removal of the hydroxy protecting groups possibly present in the product of the Wittig reaction may be carried out following known conventional procedures. For example ether residue protecting groups may be removed by mild acid hydrolysis, for instance with mono- or poly-carboxylic acids, such as, e.g., acetic, formic, citric, oxalic, or tartaric, in a solvent such as, e.g., water, acetone, tetrahydrofuran, dimethoxyethane or a low molecular weight alcohol, or with a sulfonic acid such as, e.g., p-toluenesulfonic, in a low molecular weight alcohol such as, e.g., anhydrous ethanol or methanol, or with a polystyrene-sulfonic resin. For example, a 0.1-0.25N polycarboxylic acid (like oxalic or citric) is used with a suitable low-boiling solvent miscible with water and readily removable under vacuum at the end of the reaction. Silyl ether residues may be selectively removed in the presence of other protecting groups with F⁻ions in solvents such as, e.g., tetrahydrofuran and dimethylformamide.

Ester protecting groups may be removed by following typical saponification procedures. The optional esterification of a compound of formula (I) wherein R is hydrogen to give a compound of formula (I) wherein R is $C_1$-$C_6$ alkyl optionally substituted by

wherein $R_3$ and $R_4$ are defined above may be carried out following the usual and known esterification procedures of the organic chemistry.

Thus, for example, to obtain a compound wherein $R_1$ is unsubstituted $C_1$-$C_6$ alkyl the esterfication may be carried out using the appropriate diazolkane in an inert organic solvent, e.g. diethylether, ethylacetate, methylene chloride, acetone or their mixtures at temperatures from about −10° C. to about 20° C., preferably at about 0° C.; or using the appropriate alkylhalide, for example in acetone or N,N-dimethylformamide in the presence of a base which may be, for instance, sodium or potassium carbonate or bicarbonate. To obtain a compound wherein R is $C_1$–$C_6$ alkyl substituted by a group

wherein $R_3$ and $R_4$ are as defined above, the esterification may be carried out reacting the free acid with the appropriate alcohol (i.e. aminoalcohol) in the presence of dicyclohexylcarbodiimide, or with the condensation product between the alcohol and dicyclohexylcarbodiimide, in an inert organic solvent such as, e.g., tetrahydrofuran, chloroform, methylane chloride, preferably in the presence of a base, e.g. sodium bicarbonate or pyridine.

Also the optical saponification of a compound of formula (111) wherein R is $C_1$–$C_6$ alkyl optionally substituted as reported above may be carried out by conventional procedures, for example by reaction with an aqueous solution of an alkali metal, e.g. sodium or potassium, hydroxide or carbonate in the presence of a water miscible solvent, e.g. dioxane, tetrahydrofuran, methanol or ethanol, preferably at room temperature. The saponification product may be recovered as a salt, e.g. alkali metal salt, or, previous possible acidification, as a free acid.

The optional salification of a compound of formula (I) and the optional preparation of a free compound from its salt as well as the optional separation of a mixture of isomers into the single isomers may be carried out by usual methods known per se. In particular, for example, single isomers may be obtained from their mixture by means of, e.g., fractional crystallization from a suitable solvent or by chromatography, either thin layer, column or liquid-liquid at low, medium or high pressure. For column and thin layer chromatography, for instance, silica gel or magnesium silicate may be used as support with a solvent such as, e.g., cyclohexane, n-hexane, benzene, methylene chloride, diethyl ether, isopropyl ether, ethyl acetate or methyl acetate as the mobile phase.

Thus, for example, the above illustrated reaction between a compound (II) and a compound (III) gives a mixture of geometric isomers in that the new exocyclic double bond formed in the reaction may be Z or E; if desired, the individual geometric isomers may be separated by one of the above reported techniques.

The compounds of formula (II) may be prepared by following known procedures, for example those described for preparing the analogous compounds in the above mentioned UK Pat. No. 2012265B, UK Pat. No. 2017699B, UK Pat. No. 2013661B, and European Pat. 11591.

In particular, for example, a compound of formula (ll) may be obtained by the following steps:

(1) reaction of a compund of formula (IV)

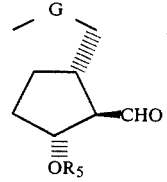

wherein $R_5$ is as defined above and G is a protected carbonyl group, with a Wittig reagent of formula (V)

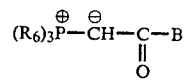

or with a modified Wittig reagent of formula (Va)

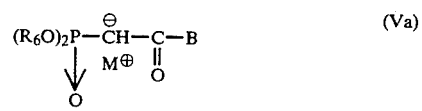

wherein B and $R_6$ are as defined above and M is a cation, to obtain a compound of formula (VI)

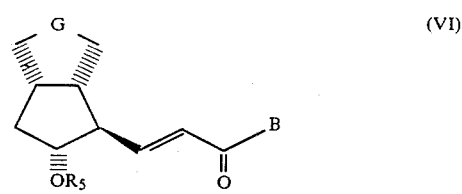

wherein G, $R_5$ and B are as defined above;

(2) halogenation of an obtained compound of formula (VI) to give a compound of formula (VII)

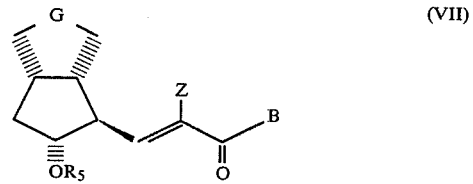

wherein G, $R_5$, Z and B are as defined above;

(3) reduction or nucleophilic addition on the free oxo group of the compound (VII) followed by separation of the obtained mixture of the S and R alcohols and optional protection of the newly formed hydroxy group, to give a compound of formula (VIII)

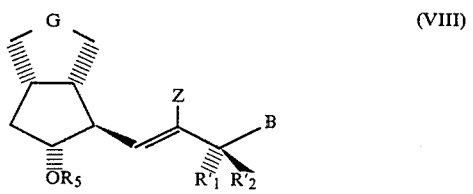

wherein G, $R_5$, Z, B, $R'_1$ and $R'_2$ are as defined above;

(4) optional dehydrohalogenation of a compound of formula (VIII) to obtain a compound of formula (VIIIa)

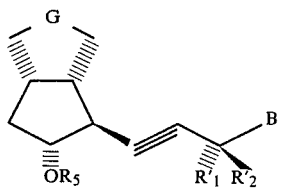

wherein G, $R_5$, B, $R'_1$ and $R'_2$ are as defined above; and (5) removal of the carbonyl protecting group from G and optional removal of the hydroxy protecting groups possibly present either in a compound of formula (VIII) or in a compound of formula (VIIIa).

In the compound of formula (IV) the protected carbonyl group G is a carbonyl group preferably protected as acetal or thioacetal, for example a dimethoxyacetal, a diethoxyacetal, a dimethylthioacetal, a diethylthioacetal, preferably a dimethoxyacetal, or as ketal or thioketal for example an ethylendioxyketal

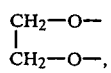

a propylendithioketal

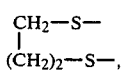

a propylendioxyketal

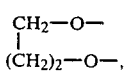

an ethylendithioketal

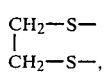

preferably an ethylendioxyketal.

In a compound of formula (V) $R_6$ is, preferably, a phenyl group. In a compound of formula (Va) $R_6$ is, preferably, a methyl group and the cation M is, preferably, an alkali metal cation, sodium or potassium in particular.

In reaction between a compound of formula (IV) and a compound of formula (V) or (Va) may be carried out using, approximately, the same reaction conditions reported above for the reaction between a compound of formula (II) and a compound of formula (III).

The halogenation of a compound of formula (VI) to give a compound of formula (VII) may be caried out following known standard procedures, for example by treatment with pyridinium bromide perbromide.

The reduction of the free oxo group in the compound of formula (VII), leading to a mixture of secondary S and R alcohols, may be performed by conventional method, e.g. by treatment with a mixed hydride such as, for instance, $NaBH_4$ or $LiAlH_4$, preferably $NaBH_4$, using the usual reaction conditions reported in the organic chemistry for this kind of reduction. The nucleophilic addition on the free oxo group of the compound of formula (VII), leading to a mixture of tertiary S and R alcohols, may be carried out in a conventional way too, for example by reaction with a Grignard reagent of formula $R_X MgZ$ wherein $R_X$ is $C_1$-$C_6$ alkyl and Z is a halogen atom as defined above, according to standard reaction conditions. The separation of the obtained mixture of either secondary or tertiary S and R alcohols may be carried out by the already indicated fractional crystallization or chromatography tecniques. The optional protection of the newly formed hydroxy group may be carried out by any known conventional etherification or esterification procedure. The optional dehydrohalogenation of a compound of formula (VIII) to give a compound of formula (VIIIa) may be performed by treatment with an appropriate base according to conventional procedures too, and standard procedures may be followed also for removing the carbonyl protecting group, and, if desired, the hydroxy protecting groups, in a compound of formula (VIII) of VIIIa). In particular, mild acid hydrolysis as reported above is preferred to remove acetal or thioacetal carbonyl protecting groups.

The compounds of formula (III) and (IV) are known compounds and may be prepared by known methods e.g. those described in UK Pat. No. 2013661B. The compounds of formula (V) and (Va) may be prepared by the same procedure used to obtain a compound of formula (III), e.g. that described in UK Pat. No. 2013661 B for the preparation of analogous compounds.

In particular, for example, a compound of formula (V) may be prepared reacting a compound of formula (IX)

wherein B is as defined above and Hal is a halogen atom, with an excess amount of a compound of formula $(R_6)_3P$ wherein $R_6$ is as defined above, triphenylphosphine for instance, in an organic solvent such as, e.g., benzene, acetonitrile or diethylether, and then treating the product phosphonium salt with an equivalent amount of an inorganic base, e.g. NaOH or KOH.

Analogously, a compound of formula (Va) may be prepared from a compound of formula (X)

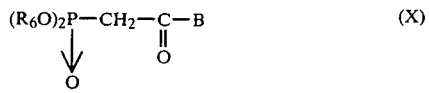

wherein $R_6$ and B are as defined above, with a suitable base caring the M+ cation, which base may be, for instance, an alkalimetal hydride such as, e.g., sodium or potassium hydride, an alkali metal alkoxide such as, e.g. sodium or potassium tert.butoxide, an alkali metal salt of a carboxyamide such as, e.g., N-sodioacetamide and N-sodiosuccinimide. The compounds of formula (IX) and (X) are in turn prepared using standard methods, for example those described by Corey et al. in J. Amer. Chem. Soc. 90, 3247 (1968) and 88, 5654 (1966). The compounds of formula (I) exhibit substantially the same pharmacological activities known for carboprostacyclins and illustrated, for instance, in the previously mentioned UK Pat. Nos. 2012265B, 2014143B, 2019847B, 2017699B, 2013661B and European Pat. No. 11591. In particular, the compounds of formula (I) show high platelet antiaggregating and disaggregating activity in that they strongly inhibit, prevent and reverse the blood platelet aggregation.

The following table reports, for example, the data concerning the platelet antiaggregating activity obtained for the compound of the invention (+) 5E-11α,15S-dihydroxy-9a-deoxy-9a-methylene-ω-pentanor-15-cyclopentyl-prostacycl-5-en-13-ynoic acid in comparison with the data obtained for the compound (+) 5E,13E-11α,15S-dihydroxy-9a-deoxy-9a-methylene-prostacycl-5,13-dienoic acid, i.e. (+) 5E-carboprostacyclin.

TABLE

| COMPOUNDS | $IC_{100}$ ng/ml |
|---|---|
| (+) 5E—carboprostacyclin | 30 |
| (+) 5E—11α,15S—dihydroxy-9a-deoxy-9a-methylene-ω-pentanor-15-cyclopentyl-prostacycl-5-en-13-ynoic acid | 2.7 |

The $IC_{100}$ reported values, represent the dose of compound which has been found to produce the 100% inhibition of the platelet aggregation induced in vitro by 0.4 μg/ml ADP in guinea pig platelet rich plasma. Precisely the data reported in the above table were obtained by the following technique: blood was drawn from the abdominal aorta of male albino guinea pigs fasted for 16 hours and of average weight 450 g, after light ether anaesthesia, using as anticoagulant a 3.8% solution of sodium citrate in distilled water (1 part sodium citrate solution and 9 parts blood).

The platelet rich plasma (PRP) of each single animal was collected by centrifugation of the blood at 1000 rpm for 8 minutes; after checking spontaneous aggregation, the PRP found suitable were combined in a single pool and the platelet count made. If necessary, the number of platelets was corrected with autologous platelet poor plasma (PPP), to obtain a PRP pool containing 750,000 platelets/mm$^3$.

Platelet aggregation was investigated with an Elvi Mod. 840 aggregometer connected to a 2-channel Servogor 2S Type RE 573 recorder. The reagents were placed in the aggregometer in the following order: 0.4 ml PRP, 0.08 ml physiological saline and 0.01 ml of solution of the test compound or solvent. After incubating at 37° C. for 5 minutes, the aggregating agent (ADP 0.4 μg/ml) was added. The aggregation tracing was monitored for 10 minutes after addition of the aggregating agent (PRP agitation speed: 800 rpm). All the dilutions of the test compound were tested on the same pool of PRP collected from 5-6 guinea pigs. The data reported in the above table clearly show that the antiaggregating activity of the compound of the invention is much greater than that of the reference compound.

The high platelet anti-aggregating and disaggregating activity exhibited by the compounds of formula (1) indicates their use to inhibit platelet aggregation, to decrease adhesions, to prevent clot formation, and to dissolve recently-formed clots. The platelet antiaggregting activity is also associated with a relaxation of the coronary arteries. Thus the compounds of formula (1) can be useful, e.g., in preventing and treating myocardial infarctions, and, in general, in treating and preventing thromboses, in treating conditions like atherosclerosis, arteriosclerosis, and, more generally, hyperlipidemia.

The compounds of the invention also exhibit a certain vasodilatory, i.e. hypotensive, effect and so they may be useful for treating the syndromes caused by arterial hypertension. While the compounds of formula (1) have particular utility as selective anti-aggregating and/or disaggregating agents and, in addition, as vasodilating, i.e. hypotensive, agents, they may also be used for treating obstructive pulmonary diseases such as, e.g., bronchial asthma, or to take advantage of their anti-ulcerogenic and antisecretory activities, as is shown, e.g. by the fact that they have been found to be active in the bronchodilation test on the awake or anaesthetized guinea-pig [Prostaglandins and Medicine vol. 2, 459–466 (1979)], in preventing ethanol-induced, stress-induced or ASA-induced gastric ulcers and indomethacin-induced intestinal ulcers [Gastroenterology 77, 761–767 (1979), and Prostaglandins and Medicine vol. 5, 131–139 (1980)], and in inhibiting gastric secretion according to the method of Shay et al. [Gastroenterology 26, 906 (1954)].

When the compounds of the invention are given as antiaggregation or disaggregating agents, the routes of administration can be the usual ones, oral, intravenous, subcutaneous, intramuscular. In emergency situations, the preferred route is intravenous, with doses that can vary, for adult humans, from 0.005 to 10 mg/kg/day. The exact dose will depend on the condition of the patient, his weight, his age and the route of administration. The dosages and methods of administration of the compounds, when used as hypotensive and vasodilatory agents, are about the same as those used for the antiaggregating application.

For the treatment of the obstructive pulmonary disorders, for example bronchial asthma, the compounds of the invention can be given by different routes: orally, in the form of tablets, capsules, coated tablets or in liquid form as drops or syrups; by inhalation, as aerosols or solutions for the nebylizer; by insufflation, in powdered form.

Doses of the order of 0.01–4 mg/kg can be given from 1 to 4 times a day to adult humans with the exact dose depending on the age, weight, and condition of the patient and on the route of administration. For use as antiasthmatics, the compounds of the invention can be combined with other antiasthmatic agents, such as sympathicomimetic drugs like isoproterenol, ephedrine, xanthine derivatives, such as theophylline and aminophylline, or corticosteroids.

For the anti-ulcerogenic and anti-secretory applications the compound of the invention can be administered, for example, by intravenous infusion or by intravenous, subcutaneous or intramuscular injection; doses for intravenous infusion range from 0.1 μg to 500 μg/kilo/minute. The total daily dose for both injection and infusion is about 0.1–20 mg/kg depending on the age, weight and condition of the patient and on the administration method. Also rectal administration and oral administration are useful for these kinds of applications.

The toxicity of the compounds of the invention, e.g. the specific one hereabove mentioned, is quite negligible, so that they can be safely used in therapy.

As previously stated, the compounds of the invention can be given, either to humans or animals, in a variety of dosage forms, e.g., orally in the form of tablets, capsules or liquids; rectally, in the form of suppositories; parenterally, subcutaneously or intramuscularly, with intravenous administration being preferred in emergency situations; by inhalation in the form of aerosols or solutions for nebulizers; in the form of sterile implants for prolonged action; or intravaginally in the form, e.g., of bougies.

As already said, the invention includes pharmaceutical and veterinary compositions containing a compound of the invention and a pharmaceutically or veterinarly acceptable carrier and/or diluent. The carrier or diluent and the form of the compositions can be any conventionally used. For example, for intravenous injection or infusion, sterile aqueous isotonic solutions are preferred. For subcutaneous or intramuscular injection, sterile solutions or suspensions in aqueous or non-aqueous media may be used; for tissue implants, a sterile tablet or silicone rubber capsule containing, or impregnated with the compound is used.

Conventional carriers or diluents are, for example, water, gelatine, lactose, dextrose, saccharose, mannitol, sorbitol, cellulose, talc, stearic acid, calcium or magnesium stearate, glycol, starch, gum arabic, tragacanth gum, alginic acid or alginates, lecithin, polysorbate, vegetable oils.

For administration by suppositories suitable carriers may be, e.g., cocoa butter, polyethylene glycol, a polyoxyethylene sorbitan fatty acid ester surfactant or lecithin.

For administration by nebulizer, a suspension or a solution of the compound of the invention, preferably in the form of a salt, such as the sodium salt in water, can be used. Alternatively, the pharmaceutical preparation can be in the form of a suspension or of a solution of the compound of the invention in one of the usual liquefied propellants, such as dichloro - difluoromethane or dichlorotetrafluorethane, administered from a pressurized container such as an aerosol bomb.

When the compound is not soluble in the propellant it may be necessary to add a cosolvent, such as ethanol, dipropylene glycol and/or surfactant, to the pharmaceutical formulation.

The abbreviations THF, DMSO and DMF used in the examples stand, respectively, for tetrahydrofuran, dimethylsulphoxide and dimethylformamide.

The following examples illustrate but do not limit in any way the invention.

EXAMPLE 1

To a solution of dimethoxymethylphosphonate (62 g) in tetrahydrofuran (500 ml) to −70° C., BuLi (0.8 moles) in n-hexane (460 ml) was added and then a 0.25 M solution of methoxycarbonylcyclohexane (35.5 g) in THF (150 ml) was added too. The reaction mixture was cooled and kept at −70° C. for 1 hour, then stirred at room temperature for 3 hours.

The solution was cooled at −10° C. and then treated with a solution of acetic acid (50 ml) in THF (50 ml), filtered and evaporated to dryness. The residue was partitioned between water and methylene chloride, the organic phase was washed, dried and distilled in vacuo. After distillation dimethyl-(2-cyclohexyl-2-oxo-ethyl)-phosphonate was recovered (36.5 g; b.p. 0.8 mmHg: 132°–134° C.).

In similar way starting from the appropriate cycloaliphatic carboxylic acid methyl esters, the following compounds were obtained:
dimethyl-(2-cyclobutyl-2-oxo-ethyl)-phosphonate;
dimethyl-(2-cyclopentyl-2-oxo-ethyl)-phosphonate;
dimethyl-[2-(3'-methyl-cyclopentyl)-2-oxo-ethyl]-phosphonate;
dimethyl-[2-(3'-ethyl-cyclopentyl)-2-oxo-ethyl]-phosphonate;
dimethyl-[2-(3'-isopropylidene-cyclopentyl)-2-oxo-ethyl]-phosphonate;
dimethyl-[2-(4'-methyl-cyclohexyl)-2-oxo-ethyl]-phosphonate;
dimethyl-[2-(4'-tert.butyl-cyclohexyl)-2-oxo-ethyl]-phosphonate;
dimethyl-[2-(4'-vinyl-cyclohexyl)-2-oxo-ethyl]-phosphonate; and
dimethyl-[2-(4'-isopropylidene-cyclohexyl)-2-oxo-ethyl]-phosphonate.

EXAMPLE 2

To a stirred suspension of triphenylmethylphosphonium iodide (118.3 g) and potassium tert. butoxide (68 g) in dry toluene (350 ml) 4-ethylcyclohexanecarboxylic acid phenoxy ester (78.9 g) was added maintaining the temperature at about 40° C. Then the mixture was refluxed for 5 hours, cooled at room temperature and treated under vigorous stirring with water (120 ml). The organic phase was washed with water then treated with acetic acid (80 ml) and with a solution of potassium iodide (80 g) in water (70 ml). Under vigorous stirring n-hexane (70 ml) was added and the precipitate was filtered obtaining trimethyl-2-oxo-2-(4'-ethylcyclohexyl)-ethylphosphonium iodide (108 g).

To a solution of this compound in water (130 ml) few drops of phenolphthalein was added and the mixture was treated under vigorous stirring with methylene chloride (130 ml) and with 1 N NaOH until weakly basic pH. The methylene chloride was separated, washed with water, dried and evaporated to dryness. The residue was taken up with diethyl ether and n-hexane (10:90) and the precipitate was filtered to give 4-ethylcyclohexylcarbonylmethylidentriphenylphosphorane.

In similar way the cyclopentylcarbonylmethylidentriphenylphosphorane was prepared.

EXAMPLE 3

A solution of 3-oxo-3,3-ethylendioxy-6-exo-formyl-7-endohydroxy-7-(2'-tetrahydropyranyloxy)-bicyclo[3.3.0]octane (6 g) in benzene (20 ml) was added to a stirred suspension of the sodium salt of dimethyl-(2-cyclohexyl-2-oxo-ethyl)-phosphonate in benzene which sodium salt was previously prepared by adding a solution of the phosphonate (6.08 g) in benzene (10 ml) to a suspension of 80% NaH (0.78 g) in benzene (100 ml).

The coupling of the aldehyde to the phosphonate was completed in 15 minutes; then the reaction mixture was washed with water, dried and evaporated to dryness.

The residue was purified by column chromatography affording 6 g of 3-oxo-3,3-ethylendioxy-6-exo-(1'-trans-3'-oxo-3'-cyclohexyl-prop-1-enyl)-7-endo-hydroxy-7-(2'-tetrahydropyranyloxy)-bicyclo[3.3.0]octane.

EXAMPLE 4

To a solution of 3,3-ethylendioxy-3-oxo-6-exo-formyl-7-endo-hydroxy-7-(2'-tetrahydropyranyloxy)-bicyclo[3.3.0]octane (3 g) in benzene (30 ml) 1.01 molar equivalents of 4-ethylcyclohexylcarbonylmethylidenetriphenylphosporane ylide were added. After 2 hours the mixture was absorbed on silica gel column and eluted with n-hexane-ethylacetate affording 3-oxo-6-exo[1'-trans-3'-oxo-3'-(4'-ethylcyclohexyl)-prop-1-enyl]-7-endo-hydroxy-7-(2'-tetrahydropyranyloxy)-bicyclo[3.3.0]octane (2.86 g).

EXAMPLE 5

Using in the procedure of the example 4 3,3-ethylendioxy-3-oxo-6-exo-formyl-7-endo-hydroxy-7-acetate-bicyclo[3.3.0]octane and the cyclopentylcarbonylmethylidentriphenylphosphorane the 3-oxo-6-exo-(1'-trans-3'-oxo-3'-cyclopentylprop-1-enyl)-7-endo-hydroxy-7-acetate-bicyclo[3.3.0]octane was obtained.

EXAMPLE 6

Using in the procedure of the example 3 the appropriate phosphonates prepared using the procedure of the example 1 the following compounds were obtained:

3-oxo-3,3-ethylendioxy-6-exo-(1'-trans-3'-oxo-3'-cyclobutyl-prop-1-enyl)-7-endo-hydroxy-7-(2'-tetrahydropyranyloxy)-bicyclo[3.3.0]octane;

3-oxo-3,3-ethylendioxy-6-exo-(1'-trans-3'-oxo-3'-cyclopentyl-prop-1-enyl)-7-endo-hydroxy-7-(2'-tetrahydropyranyloxy)-bicyclo[3.3.0]octane;

3-oxo-3,3-ethylendioxy-6-exo{1'-trans-3'-oxo-3'-[(3''-methyl)-cyclopentyl]-prop-1-enyl}-7-endo-hydroxy-7-(2'-tetrahydropyranyloxy)-bicyclo[3.3.0]octane;

3-oxo-3,3-ethylendioxy-6-exo-{1'-trans-3'-oxo-3'-[(3''-ethylcyclopentyl]-prop-1-enyl}-7-endo-hydroxy-7-(2'-tetrahydropyranyloxy)-bicyclo[3.3.0]octane;

3-oxo-3,3-ethylendioxy-6-exo-{1'-trans-3'-oxo-3'-[(3''-isopropylidene)-cyclopentyl]-prop-1-enyl}-7-endo-hydroxy-7-(2'-tetrahydropyranyloxy)-bicyclo[3.3.0]octane;

3-oxo-3,3-ethylendioxy-6-exo-{1'-trans-3'-oxo-3'-[(4''-methyl)-cyclohexyl]prop-1-enyl}-7-endo-hydroxy-7-(2'-tetrahydropyranyloxy)-bicyclo[3.3.0]octane;

3-oxo-3,3-ethylendioxy-6-exo-{1'-trans-3'-oxo-3'-[(4''-tert.butyl)-cyclohexyl]prop-1-enyl}-7-endo-hydroxy-7-(2'-tetrahydropyranyloxy)-bicyclo[3.3.0]octane;

3-oxo-3,3-ethylendioxy-6-exo-{1'-trans-3'-oxo-3'-[(4''-vinyl)-cyclohexyl]prop-1-enyl}-7-endo-hydroxy-7-(2'-tetrahydropyranyloxy)-bicyclo[3.3.0]octane;

3-oxo-3,3-ethylendioxy-6-exo-{1'-trans-3'-oxo-3'-[(4''-isopropylidene)-cyclohexyl]prop-1-enyl}-7-endo-hydroxy-7-(2'-tetrahydropyranyloxy)-bicyclo[3.3.0]octane.

EXAMPLE 7

A solution of 3-oxo-3,3-ethylendioxy-6-exo-(1'-trans-3'-oxo-3'-cyclohexylprop-1'-enyl)-7-hydroxy-7-(2tetrahydropyranyloxy)bicyclo[3.3.0]octane (4 g) in pyridine (40 ml) was treated under stirring with pyridinehydrotribromide (4.8 g) for 2 hours. The mixture was diluted with aqueous 30% NaH$_2$PO$_4$ solution (250 ml) and exaustively extracted with ethylacetate. The collected organic phases were washed with water, dried and evaporated to dryness. After SiO$_2$ column chromatography (n-hexane-ethylacetate 70:30) 2.5 g of 3-oxo-3,3-ethylendixoy-6-exo-(1'-trans-2'-bromo-3'-oxo-3'-cyclohexyl-prop-1'-enyl)-7-hydroxy-7-(2''-tetrahydropyranyloxy)-bicyclo[3.3.0]octane were obtained.

Using analogous procedure the following compounds were obtained:

3-oxo-3,3-ethylendioxy-6-exo-(1'-trans-2'-bromo-3'-oxo-3'-cyclopentyl-prop-1'-enyl)-7-hydroxy-7-(2''-tetrahydropyranyloxy)-bicyclo[3.3.0]octane;

3-oxo-3,3-ethylendioxy-6-exo-{1'-trans-2'-bromo-3'-oxo-3'-[(3''-methyl)-cyclopentyl]-prop-1'-enyl}-7-hydroxy-7-(2''-tetrahydropyranyloxy)-bicyclo[3.3.0]octane;

3-oxo-3,3-ethylendioxy-6-exo-{1'-trans-2'-bromo-3'-oxo-3'-[(3''-ethyl-cyclopentyl]-prop-1'-enyl}-7-hydroxy-7-(2'''-tetrahydropyranyloxy)-bicyclo[3.3.0]octane;

3-oxo-3,3-ethylendioxy-6-exo-{1'-trans-2'-bromo-3'-oxo-3'-[(3''-isopropylidene)-cyclopentyl]-prop-1'-enyl}-7-hydroxy-7-(2''-tetrahydropyranyloxy)-bicyclo[3.3.0]octane;

3-oxo-3,3-ethylendioxy-6-exo-{1'-trans-2'-bromo-3'-oxo-3'-[(4''-methyl)-cyclohexyl]prop-1'-enyl}-7-hydroxy-7-(2''-tetrahydropyranyloxy)-bicyclo[3.3.0]octane;

3-oxo-3,3-ethylendioxy-6-exo-{1'-trans-2'-bromo-3'-oxo-3'-[(4''-tert.butyl)-cyclohexyl]prop-1'-enyl}-7-hydroxy-7-(2''-tetrahydropyranyloxy)-bicyclo[3.3.0]octane;

3-oxo-3,3-ethylendioxy-6-exo-{1'-trans-2'-bromo-3'-oxo-3'-[(4''-ethyl)-cyclohexyl]prop-1'-enyl}-7-hydroxy-7-(2''-tetrahydropyranyloxy)-bicyclo[3.3.0]octane;

3-oxo-3,3-ethylendioxy-6-exo-(1'-trans-2'-bromo-3'-oxo-3'-cyclopentyl-prop-1'-enyl)-7-hydroxy-7-acetate-bicyclo[3.3.0]octane and the 7-acetate derivatives of the other hereabove mentioned compounds.

EXAMPLE 8

A solution of 3-oxo-3,3-ethylendioxy-6-exo-{1'-trans-3'-oxo-3'-[(4''-vinyl)-cyclohexyl]-prop-1'-enyl}-7-hydroxy-7-(2'-tetrahydropyranyloxy)-bicyclo[3.3.0]octane (4 g) in pyridine (40 ml) was treated with 2.2 molar equivalents of pyridinehydrotribromide for 2 hours. The reaction mixture was diluted with an aqueous 30% NaH$_2$PO$_4$ solution, extracted with ethyl acetate, washed with water until neutral and dried. The solvent was evaporated in vacuo and the residue was dissolved in acetone and treated for 12 hours at room temperature with an excess of sodium iodide (10 g). The red solution was treated with 1 N aqueous sodium thiosulphate till decolourization diluted with water, extracted with ethyl acetate and after usual work-up and SiO$_2$ gel chromatography 3-oxo-3,3-ethylendioxy-6-exo-{1'-trans-2'-bromo-3'-oxo-3'-[(4''-vinyl)-cyclohexyl]-prop-1'-enyl}-7-hydroxy-7-(2'-tetrahydropyranyloxy)-bicyclo[3.3.0]octane (1.82 g) was obtained.

In similar way the compound 3-oxo-3,3-ethylendioxy-6-exo-{1'-trans-2'-bromo-3'oxo-3'-[(4''-isopropylidene)-cyclohexyl]-prop-1'-enyl}-7-hydroxy-7-(2'-tetrahydropyranyloxy)-bicyclo[3.3.0]octane was obtained.

EXAMPLE 9

To a stirred solution of NaBH$_4$ (0.75 mg) in MeOH (30 ml) cooled at $-10°$ C. a solution of 3-oxo-3,3-ethylendioxy-6-exo-(1'-trans-2'-bromo-3'-oxo-3'-cyclohexyl-prop-1'-enyl)-7-hydroxy-7-(2'-tetrahydropyranyloxy)-bicyclo[3.3.0]octane (2.5 g) in MeOH (15 ml) was added. After 1 hour the reaction mixture was diluted with 30% aqueous NaH$_2$PO$_4$ (200 ml) and extracted with ethylacetate. The organic phases were collected, dried and, after evaporation in vacuo of the solvent, the residue was taken up with acetone (20 ml). After addition of aqueous 1N oxalic acid solution (20 ml) the mixture was heated at 40° C. for 15 hours. Then the acetone was removed in vacuo, the aqueous emulsion was extracted with ethylacetate. The organic extracts were collected, washed with water, dried over MgSO$_4$ and the solvent was evaporated. The residue was chromatographed on silica gel with ethylacetate:n-hexane 80:20, affording in the order 3-oxo-6-exo-(1'-trans-2'-bromo-3'R-hydroxy-3'-cyclohexyl-prop-1'-enyl)-7-endohydroxy-bicyclo[3.3.0]octane (0.48 g) and 3-oxo-6-exo-(1'-trans-2'-bromo-3'S-hydroxy-3'-cyclohexyl-prop-1'-enyl)-7-endo-hydroxy-bicyclo[3.3.0]octane (0.88 g).

EXAMPLE 10

Using in the procedure of the example 9 the α-bromo-α,β-unsaturated ketones obtained in the examples 7 and 8 the following bromo-allylic alcohols were obtained:

3-oxo-6-exo-(1'-trans-2'-bromo-3'S-hydroxy-3'-cyclopentyl-prop-1'-enyl)-7-endo-hydroxy-bicyclo[3.3.0]octane;

3-oxo-6-exo-}1'-trans-2'-bromo-3'S-hydroxy-3'-[3"-methyl)-cyclopentyl]-prop-1'enyl}-7-endo-hydroxy-bicyclo[3.3.0]octane;

3-oxo-6-exo-}1'-trans-2'-bromo-3'S-hydroxy-3'-[(3"-ethyl)-cyclopentyl]-prop-1'-enyl}-7-endo-hydroxy-bicyclo[3.3.0]octane;

3-oxo-6-exo-{1'-trans-2'-bromo-3'S-hydroxy-3'-[(3"-isopropylidene)-cyclopentyl]-prop-1'-enyl}-7-endo-hydroxy-bicyclo [3.3.0]octane;

3-oxo-6-exo-(1'-trans-2'-bromo-3'S-hydroxy-3'-cyclobutyl-prop-1'-enyl)-7-endo-hydroxy-bicyclo[3.3.0]octane;

3-oxo-6-exo-{1'-trans-2'-bromo-3'S-hydroxy-3'-[(4"-methyl)-cyclohexyl]-prop-1'-enyl}-7-endo-hydroxy-bicyclo[3.3.0]octane;

3-oxo-6-exo-{1'-trans-2'-bromo-3'S-hydroxy-3'-[(4"-ethyl)-cyclohexyl]-prop-1'-enyl}-7-endo-hydroxy-bicyclo[3.3.0]octane;

3-oxo-6-exo-{1'-trans-2'-bromo-3'S-hydroxy-3'-[(4"-t-butyl)-cyclohexyl]-prop-1'-enyl}-7-endo-hydroxy-bicyclo[3.3.0]octane;

3-oxo-6-exo-{1'-trans-2'-bromo-3'S-hydroxy-3'-[(4"-vinyl)-cyclohexyl]-prop-1'-enyl}-7-endo-hydroxy-bicyclo[3.3.0]octane;

3-oxo-6-exo-{1'-trans-2'-bromo-3'S-hydroxy-3'-[(4"-isopropylidene)-cyclohexyl]-prop-1'-enyl}-7-endo-hydroxy-bicyclo[3.3.0]octane;

3-oxo-6-exo-(1'-trans-2'-bromo-3'S-hydroxy-3'-cyclopentyl-prop-1'-enyl)-7-endo-hydroxy-7-acetate-bicyclo[3.3.0]octane;

3oxo-6-exo-{1'-trans-2'-bromo-3'S-hydroxy-3'[(3"-methyl)-cyclopentyl]-prop-1'-enyl}-7-endo-hydroxy-7-acetate-bicyclo [3.3.0[octane;

3-oxo-6-exo-{1'-trans-2'-bromo-3'S-hydroxy-3-S-hydroxy-3'[(3"-ethyl)-cyclopentyl]-prop-1'-enyl}-7-endo-hydroxy-7-acetate-bicyclo[3.3.0]octane;

3-oxo-6-exo }1'-trans-2'-bromo-3'S-hydroxy-3'[(3"-isopropylidene)-cyclopentyl]-prop-1'enyl}-7-endo-hydroxy-7-acetate-bicyclo[3.3.0]octane;

3-oxo-6-exo-(1'-trans-2'-bromo-3'S-hydroxy-3'-cyclobutyl-prop-1'-enyl)-7-endo-hydroxy-7-acetate-bicyclo[3.3.0]octane;

3-oxo-6-exo-{1'-trans-2'-bromo-3'S-hydroxy-3'-[(4"-methyl)-cyclohexyl]-prop-1'-enyl}-7-endo-hydroxy-7-acetate-bicyclo[3.3.0]octane;

3-oxo-6-exo-{1'-trans-2'-bromo-3'S-hydroxy-3'-[(4"-ethyl}-cyclohexyl]-prop-1'-enyl}-7-endo-hydroxy-7-acetate-bicyclo[3.3.0]octane;

3-oxo-6-exo-{1'-trans-2'-bromo-3'S-hydroxy-3'-[(4"-t-butyl)-cyclohexyl]-prop-1'-enyl}-7-endo-hydroxy-7-acetate-bicyclo[3.3.0]octane;

3-oxo-6-exo-{1'-trans-2'-bromo-3'S-hydroxy-3'-[(4"-vinyl)-cyclohexyl]-prop-1'-enyl}-7-endo-hydroxy-7-acetate-bicyclo[3.3.0]octane;

3-oxo-6-exo-{1'-trans-2'-bromo-3'S-hydroxy-3'-[(4"-isopropylidene)-cyclohexyl]-prop-1'-enyl}-7-endo-hydroxy-7-acetate-bicyclo[3.3.0]octane;

3-oxo-6-exo-(1'-trans-2'-bromo-3'R-hydroxy-3'-cyclopentyl-prop-1'-enyl)-7-endo-hydroxy-bicyclo[3.3.0]octane;

3-oxo-6-exo-{1'-trans-2'-bromo-3'R-hydroxy-3'-[(3"-methyl)-cyclopentyl]-prop-1'-enyl}-7-endo-hydroxy-bicyclo[3.3.0]octane;

3-oxo-6-exo-{1'-trans-2'-bromo-3'R-hydroxy-3'-[(3"-ethyl)-cyclopentyl]-prop-1'-enyl}-7-endo-hydroxy-bicyclo[3.3.0]octane;

3-oxo-6-exo-{1'-trans-2'-bromo-3'R-hydroxy-3'-[(3"-isopropylidene)-cyclopentyl]-prop-1'-enyl}-7-endo-hydroxy-bicyclo[3.3.0]octane;

3-oxo-6-exo-(1'-trans-2'-bromo-3'R-hydroxy-3'-cyclobutyl-prop-1'-enyl)-7-endo-hydroxy-bicyclo[3.3.0]octane;

3-oxo-6-exo-{1'-trans-2'-bromo-3'R-hydroxy-3'-[(4"-methyl)-cyclohexyl]-prop-1'-enyl}-7-endo-hydroxy-bicyclo[3.3.0]octane;

3-oxo-6-exo-{1'-trans-2'-bromo-3'R-hydroxy-3'-[(4"-ethyl)-cyclohexyl]-prop-1'-enyl}-7-endo-hydroxy-bicyclo[3.3.0]octane;

3-oxo-6-exo-{1'-trans-2'-bromo-3'R-hydroxy-3'-[(4"-t-butyl)-cyclohexyl]-prop-1'-enyl}-7-endo-hydroxy-bicyclo[3.3.0]octane;

3-oxo-6-exo-{1'-trans-2'-bromo-3'R-hydroxy-3'-[(4"-vinyl)-cyclohexyl]-prop-1'-enyl}-7-endo-hydroxy-bicyclo[3.3.0]octane;

3-oxo-6-exo-{1'-trans-2'-bromo-3'R-hydroxy-3'-[(4"-isopropylidene)-cyclohexyl]-prop-1'-enyl}-7-endo-hydroy-bicyclo[3.3.0]octane;

3-oxo-6-exo-(1'-trans-2'-bromo-3'R-hydroxy-3'-cyclopentyl-prop-1'-enyl)-7-endo-hydroxy-7-acetate-bicyclo[3.3.0]octane;

3-oxo-6-exo-{1'-trans-2'-bromo-3'R-hydroxy-3'-[(3"-methyl)-cyclopentyl]-prop-1'-enyl}-7-endo-hydroxy-7-acetate-bicyclo[3.3.0]octane;

3-oxo-6-exo-{1'-trans-2'-bromo-3'R-hydroxy-3'-[(3"-ethyl)-cyclopentyl]-prop-1'-enyl}-7-endo-hydroxy-7-acetate-bicyclo[3.3.0]octane;

3-oxo-6-exo-{1'-trans-2'-bromo-3'R-hydroxy-3'-[(3"-isopropylidene)-cyclopentyl]-prop-1'-enyl}-7-endo-hydroxy-7-acetate-bicyclo[3.3.0]octane;

3-oxo-6-exo-(1'-trans-2'-bromo-3'R-hydroxy-3'-cyclobutyl-prop-1'-enyl)-7-endo-hydroxy-7-acetate-bicyclo[3.3.0]octane;

3-oxo-6-exo-{1'-trans-2'-bromo-3'R-hydroxy-3'-[(4"-methyl)-cyclohexyl]-prop-1'-enyl}-7-endo-hydroxy-7-acetate-bicyclo[3.3.0]octane;

3-oxo-6-exo-{1'-trans-2'-bromo-3'R-hydroxy-3'-[(4"-ethyl)-cyclohexyl]-prop-1'-enyl}-7-endo-hydroxy-7-acetate-bicyclo[3.3.0]octane;

3-oxo-6-exo-{1'-trans-2'-bromo-3'R-hydroxy-3'-[(4"-t-butyl)-cyclohexyl]-prop-1'-enyl}-7-endo-hydroxy-7-acetate-bicyclo[3.3.0]octane;

3-oxo-6-exo-{1'-trans-2'-bromo-3'R-hydroxy-3'-[(4"-vinyl)-cyclohexyl]-prop-1'-enyl}-7-endo-hydroxy-7-acetate-bicyclo[3.3.0]octane;

3-oxo-6-exo-{1'-trans-2'-bromo-3'R-hydroxy-3'-[(4"-isopropylidene)-cyclohexyl]-prop-1'enyl}-7-endo-hydroxy-7-acetate-bicyclo[3.3.0]octane.

EXAMPLE 11

Under nitrogen atmosphere 4-carboxy-butyl-triphenyl-phosphonium bromide (6.5 g) was added to a mixture of potassium tert.butoxide (3.2 g) and DMSO (32 ml); then this mixture was treated with a solution of 3-oxo-6-exo-(1'-trans-2'-bromo-3'-cyclohexyl-3'S-hydroxy-prop-1'-enyl)-7-hydroxy-bicyclo[3.3.0]octane (0.88 g) in DMSO (3 ml). After 3 hours the reaction mixture was diluted with water, acidified with 2N H$_2$SO$_4$ and extracted with diethyl ether. The ethereal phase was extracted with 1N NaOH aqueous solution; the aqueous alkaline extracts were collected; acidified to pH 5 and extracted with n-pentane-diethyl ether (20:80). The final organic extracts were collected, washed with water, dried and evaporated to dryness. The residue was chromatographed on silica gel [eluent: diethyl ether (100 ml) acetic acid (0.4 ml)] so obtaining in the order 5Z-11α,15S-dihydroxy-9a-deoxy-9a-methylene-ω-pentanor-15-cyclohexyl-prostacycl-5-en-13-ynoic acid (0.12 g), NMR (CDCl$_3$) δ p.p.m.: 5.27 (1H, t) H$_5$; 4.17 (1H, d) H$_{15}$; 4.00 (1H, m) H$_{11}$; and 5E-11α,15S-dihydroxy-9a-deoxy-9a-methylene-ω-pentanor-15-cyclohexyl-prostacycl-5-en-13-ynoic acid (0.18 g), NMR (CDCl$_3$) δ p.p.m.: 5.26 (1H, t) H$_5$; 4.17 (1H, d) H$_{15}$; 4.01 (1H, m) H$_{11}$.

By proceeding analogously the following compounds were obtained:

5E-11α,15S-dihydroxy-9a-deoxy-9a-methylene-ω-pentanor-15-cyclobutyl-prostacycl-5-en-13-ynoic acid;

5E-11α,15S-dihydroxy-9a-deoxy-9a-methylene-ω-pentanor-15-[(4'-methyl)-cyclohexyl]-prostacycl-5-en-13-ynoic acid, NMR (CDCl$_3$)δp.p.m.: 0.98 (3H,d); 3.99 (1H,m); 4.19 (1H, broad d); 5.25 (1H,m);

5E-11α,15S-dihydroxy-9a-deoxy-9a-methylene-ω-pentanor-15-[(4'-ethyl)-cyclohexyl]-prostacycl-5-en-ynoic acid, NMR (CDCl$_3$)δp.p.m.: 0.91 (3H,d); 1.31 (2H,m); 3.95(1H,m); 4.21 (1H, broad d); 5.27 (1H,m);

5E-11α,15S-dihydroxy-9a-deoxy-9a-methylene-ω-pentanor-15-[(4'-tert.butyl)-cyclohexyl]-prostacycl-5-en-13-ynoic acid;

5E-11α,15S-dihydroxy-9a-deoxy-9a-methylene-ω-pentanor-15-[(4'-vinyl)-cyclohexl]-prostacycl-5-en-13-ynoic acid;

5E-11α,15S-dihydroxy-9a-deoxy-9a-methylene-ω-pentanor-15-[(4'-isopropylidene)-cyclohexyl]-prostacycl-5-en-13-ynoic-acid, NMR (CDCl$_3$)δp.p.m.: 1.70 (6H,s); 4.01 (1H,m); 4.22 (1H, broad d); 5.27 (1H,m);

5Z-11α,15S-dihydroxy-9a-deoxy-9a-methylene-ω-pentanor-15-cyclobutyl-prostacycl-5-en-13-ynoic acid;

5Z-11α,15S-dihydroxy-9a-deoxy-9a-methylene-ω-pentanor-15-[(4'-methyl)-cyclohexyl]-prostacycl-5-en-13-ynoic acid, NMR (CDCl$_3$)δp.p.m.: 0.98 (3H,d); 3.99 (1H,m); 4.19 (1H,broad d); 5.26 (1H,m);

5Z-11α,15S-dihydroxy-9a-deoxy-9a-methylene-ω-pentanor-15-[(4'-ethyl)-cyclohexyl]-prostacycl-5-en-13-ynoic acid, NMR (CDCl$_3$)δp.p.m.: 0.91 (3H,d); 1.31 (2H,m); 3.95 (1H,m); 4.21 (1H,broad d); 5.28 (1H,m);

5Z-11α,15S-dihydroxy-9a-deoxy-9a-methylene-ω-pentanor-15-[(4'-tert.butyl)-cyclohexyl]-prostacycl-5-en-13-ynoic acid;

5Z-11α,15S-dihydroxy-9a-deoxy-9a-methylene-ω-pentanor-15-[(4'-vinyl)-cyclohexyl]-prostacycl-5-en-13-ynoic acid;

5Z-11α,15S-dihydroxy-9a-deoxy-9a-methylene-ω-pentanor-15-[(4'-isopropylidene)-cyclohexyl]-prostacycl-5-en-13-ynoic acid, NMR (CDCl$_3$)δp.p.m.: 1.70 (6H,s); 4.01 (1H,m); 2.22 (1H,broad d); 5.28 (1H,m);

5(Z,E)-11α,15S-dihydroxy-9a-deoxy-9a-methylene-ω-pentanor-15-cyclobutyl-prostacycl-5-en-13-ynoic acid;

5(Z,E)-11α,15S-dihydroxy-9a-deoxy-9a-methylene-ω-pentanor-15-[(4'-methyl)-cyclohexyl]-prostacycl-5-en-13-ynoic acid;

5(Z,E)-11α,15S-dihydroxy-9a-deoxy-9a-methylene-ω-pentanor-15-[(4'-ethyl)-cyclohexyl]-prostacycl-5-en-13-ynoic acid;

5(Z,E)-11α,15S-dihydroxy-9a-deoxy-9a-methylene-ω-pentanor-15-[(4'-tert.butyl)-cyclohexyl]-prostacycl-5-en-13-ynoic acid;

5(Z,E)-11α,15S-dihydroxy-9a-deoxy-9a-methylene-ω-pentanor-15-[(4'-vinyl)-cyclohexyl]-prostacycl-5-en-13-ynoic acid;

5(Z,E)-11α,15S-dihydroxy-9a-deoxy-9a-methylene-ω-pentanor-15-[(4'-isopropylidene)-cyclohexyl]-prostacycl-5-en-13-ynoic acid; and 5(Z,E)-11α,15S-dihydroxy-9a-deoxy-9a-methylene-ω-pentanor-15-cyclohexyl-prostacycl-5-en-13-ynoic acid.

EXAMPLE 12

Under nitrogen atmosphere 4-carboxy-butyl-triphenyl-phosphonium bromide (6.5 g) was added to a mixture of potassium tert.butoxyde (3.2 g) and DMSO (32 ml); then this mixture was treated with a solution of 3-oxo-6-exo-(1'-trans-2'-bromo-3'-cyclopentyl-3'S-hydroxy-prop-1'-enyl)-7-hydroxy-bicyclo[3.3.0]octane (0.84 g) in DMSO (3 ml).

After 3 hours the reaction mixture was diluted with water, acidified with 2N H$_2$SO$_4$ and extracted with diethyl ether.

The ethereal phase was extracted with 1N NaOH aqueous solution; the aqueous alkaline extracts were collected; acidified to pH 5 and extracted with n-pentane:diethyl ether (20:80). The final organic extracts were collected, washed with water, dried and evaporated to dryness.

The residue containing 5(Z,E)-11α,15S-dihydroxy-9a-deoxy-9a-methylene-ω-pentanor-15 -cyclopentyl-prostacycl-5-en-13-ynoic acid was chromatographed on silica gel [eluant: diethyl ether (100 ml) acetic acid (0.4 ml)] so obtaining in the order 5Z-11α, 15S-dihydroxy-9a-dexoy-9a-methylene-ω-pentanor-15 -cyclopentyl-prostacycl-5-en-13-ynoic acid (0.10 g), NMR (CDCl$_3$)δp.p.m: 3.93 (1H, broad m); 4.22 (1H, broad d); 4.55 (3H, broad m); 5.24 (1H, m); and 5E-11α,15S-dihydroxy-9a-deoxy-9a-methylene-ω-pentanor-15-cyclopentyl-prostacycl-5-en-13-ynoic acid (0.17 g), NMR (CDCl$_3$)δp.p.m.: 3.93 (1H,broad m); 4.22 (1H, broad d); 4.55 (3H, broad m); 5.22 (1H, m).

By analogous procedure the following compounds were obtained:

5(Z,E)-11α,15S-dihydroxy-9a-deoxy-9a-methylene-ω-pentanor-15-[(3'-methyl)-cyclopentyl]-prostacycl-5-en-13-ynoic acid;

5(Z,E)-11α,15S-dihydroxy-9a-deoxy-9a-methylene-ω-pentanor-15-[(3'-ethyl)-cyclopentyl]-prostacycl-5-en-13-ynoic acid;

5(Z,E)-11α,15S-dihydroxy-9a-deoxy-9a-methylene-ω-pentanor-15-[(3'-tert.butyl)-cyclopentyl]-prostacycl-5-en-13-ynoic acid;

5(Z,E)-11α,15S-dihydroxy-9a-deoxy-9a-methylene-ω-pentanor-15-[(3'-vinyl)-cyclopentyl]-prostacyl-5-en-13-ynoic acid;

5(Z,E)-11α,15S-dihydroxy-9a-deoxy-9a-methylene-ω-pentanor-15-[(3'-isopropylidene)-cyclopentyl]-prostacycl-5-en-13-ynoic acid;

5E-11α,15S-dihydroxy-9a-deoxy-9a-methylene-ω-pentanor-15-[(3'-methyl)-cyclopentyl]-prostacycl-5-en-13-ynoic acid; NMR (CDCl$_3$)δp.p.m: 0.97 (3H, d); 3.97 (1H,m); 4.20 (1H, broad d); 5.24 (1H, m);

5E-11α,15S-dihydroxy-9a-deoxy-9a-methylene-ω-pentanor-15-[(3'-ethyl)-cyclopentyl]-prostacycl-5en-13-ynoic acid; NMR (CDCl₃)δp.p.m: 0.93 (3H,d); 1.33 (2H,m); 3.94 (1H,m); 4.17 (1H,broad d); 5.25 (1H,m);

5E-11α,15S-dihydroxy-9a-deoxy-9a-methylene-ω-pentanor-15-[(3'-tert.butyl)-cyclopentyl]-prostacycl-5-en-13-ynoic acid;

5E-11α,15S-dihydroxy-9a-deoxy-9a-methylene-ω-pentanor-15-[(3'-vinyl)-cyclopentyl]-prostacycl-5-en-13-ynoic acid;

5E-11α,15S-dihydroxy-9a-deoxy-9a-methylene-ω-pentanor-15-[(3'-isopropylidene)-cyclopentyl]-prostacycl-5-en-13-ynoic acid, NMR (CDCl₃)δp.p.m: 1.70 (6H,s); 4.03 (1H,m); 4.22 (1H, broad d); 5.27 (1H,m);

5Z-11α,15S-dihydroxy-9a-deoxy-9a-methylene-ω-pentanor-15-[(3'-methyl)-cyclopentyl]-prostacycl-5-en-13-ynoic acid; NMR (CDCl₃)δp.p.m: 0.97 (3H, d); 3.97 (1H, m); 4.20 (1H,broad d); 5.25 (1H, m);

5Z-11α,15S-dihydroxy-9a-deoxy-9a-methylene-ω-pentanor-15-[(3'-ethyl)-cyclopentyl]-prostacycl-5-en-13-ynoic acid; NMR (CDCl₃)δp.p.m: 0.93 (3H, d); 1.33 (2H, m); 3.94 (1H, m); 4.17 (1H,broad d); 5.26 (1H,m);

5Z-11α,15S-dihydroxy-9a-deoxy-9a-methylene-ω-pentanor-15-[(3'-tert.butyl)-cyclopentyl]-prostacycl-5-en-13-ynoic acid;

5Z-11α,15S-dihydroxy-9a-deoxy-9a-methylene-ω-pentanor-15-[(3'-vinyl)-cyclopentyl]-prostacycl-5-en-13-ynoic acid;

5Z-11α,15S-dihydroxy-9a-deoxy-9a-methylene-ω-pentanor-15-[(3'-isopropylidene)-cyclopentyl]-prostacycl-5-en-13-ynoic acid, N.M.R. (CDCl₃)δp.p.m: 1.70 (6H, s); 4.03 (1H,m); 4.22 (1H, broad d); 5.28 (1H, m).

EXAMPLE 13

Under nitrogen atmosphere 4-carboxy-butyl-triphenyl-phosphonium bromide (6.5 g) was added to a mixture of potassium tert.butoxyde (3.2 g) and DMSO (32 ml); then this mixture was treated with a solution of (+)3-oxo-6-exo-(1'-trans-2'-bromo-3'-cyclopentyl-3'S-hydroxy-prop-1'-enyl)-7-hydroxy-bicyclo[3.3.0]octane (0.84 g) in DMSO (3 ml).

After 3 hours the reaction mixture was diluted with water, acidified with 2N H₂SO₄ and extracted with diethyl ether. The ethereal phase was extracted with 1N NaOH aqueous solution; the aqueous alkaline extracts were collected; acidified to pH 5 and extracted with n-pentane:diethyl ether (20:80). The final organic extracts were collected, washed with water, dried and evaporated to dryness.

The residue containing (+)5(Z,E)-11α,15S-dihydroxy-9a-deoxy-9a-methylene-ω-pentanor-15-cyclopentyl-prostacycl-5-en-13-ynoic acid was chromatographed on silica gel [eluant: diethyl ether (100 ml) acetic acid (0.4 ml)] so obtaining in the order (+)5Z-11α,15S-dihydroxy-9a-deoxy-9a-methylene-ω-pentanor-15-cyclopentyl-prostacycl-5-en-13-ynoic acid (0.11 g), NMR (CDCl₃)δp.p.m.: 3.93 (1H, broad m); 4.22 (1H, broad d); 4.55 (3H, broad m); 5.23 (1H,m); and (+) 5E-11α,15S-dihydroxy-9a-deoxy-9a-methylene-ω-pentanor-15-cyclopentyl-prostacycl-5-en-13-ynoic acid (0.17 g), NMR (CDCl₃)δp.p.m.: 3.93 (1H, broad m); 4.22 (1H, broad d); 4.55 (3H, broad m); 5.22 (1H, m).

By analogous procedure the following compounds were obtained:

(+)5(Z,E)-11α,15S-dihydroxy-9a-deoxy-9a-methylene-ω-pentanor-15-[(3'-methyl)-cyclopentyl]-prostacycl-5-en-13-ynoic acid;

(+) 5(Z,E)-11α,15S-dihydroxy-9a-deoxy-9a-methylene-ω-pentanor-15-[(3'-ethyl)-cyclopentyl]-prostacycl-5-en-13-ynoic acid;

(+)5(Z,E)-11α,15S-dihydroxy-9a-deoxy-0a-methylene-ω-pentanor-15-[(3'-tert.butyl)-cyclopentyl]-prostacycl-5-en-13-ynoic acid; (+)5(Z,E)-11α,15S-dihydroxy-9a-deoxy-9a-methylene-ω-pentanor-15-[(3-vinyl)-cyclopentyl]-prostacycl-5-en-13-ynoic acid;

(+)5(Z,E)-11α,15S-dihydroxy-9a-deoxy-9a-methylene-ω-pentanor-15-[(3'-isopropylidene)-cyclopentyl]-prostacycl-5-en-13-ynoic acid;

(+)5E-11α,15S-dihydroxy-9a-deoxy-9a-methylene-ω-pentanor-15-[(3'-methyl)-cyclopentyl]-prostacycl-5-en-13-ynoic acid; NMR (CDCl₃)δp.p.m: 0.97 (3H, d); 3.97 (1H,m); 4.20 (1H, broad d); 5.24 (1H,m);

(+)5E-11α,15S-dihydroxy-9a-deoxy-9a-methylene-ω-pentanor-15-[(3'-ethyl)-cyclopentyl]-prostacycl-5-en-13-ynoic acid; NMR (CDCl₃)δp.p.m: 0.93 (1H,d); 1.33 (2H,m); 3.94 (1H, m); 4.17 (1H, broad d); 5.25 (1H,m);

(+)5E-11α,15S-dihydroxy-9a-deoxy-9a-methylene-ω-pentanor-15-[(3'-tert.butyl)-cyclopentyl]-prostacycl-5-en-13-ynoic acid;

(+) 5E-11α,15S-dihydroxy-9a-deoxy-9a-methylene-ω-pentanor-15-[(3'-vinyl)-cyclopentyl]-prostacycl-5-en-13-ynoic acid;

(+) 5E-11α,15S-dihydroxy-9a-deoxy-9a-methylene-ω-pentanor-15-[(3'-isopropylidene)-cyclopentyl]-prostacycl-5-en-13-ynoic acid, NMR (CDCl₃)δp.p.m: 1.70 (6H,s); 4.03 (1H,m); 4.22 (1H, broad d): 5.27 (1H,m);

(+) 5Z-11α,15S-dihydroxy-9a-deoxy-9a-methylene-ω-pentanor-15-[(3'-methyl)-cyclopentyl]-prostacycl-5-en-13-ynoic acid, NMR (CDCl₃)δp.p.m: 0.97 (3H, d); 3.97 (1H, m); 4.20 (1H, broad d); 5.25 (1H, m);

(+)5Z-11α,15S-dihydroxy-9a-deoxy-9a-methylene-ω-pentanor-15-[(3'-ethyl)-cyclopentyl]-prostacycl-5-en-13-ynoic acid, NMR (CDCl₃)δp.p.m: 0.93 (3H, d); 1.33 (2H, m); 3.94 (1H, m); 4.17 (1H, broad d); 5.26 (1H, m);

(+)5Z-11α,15S-dihydroxy-9a-deoxy-9a-methylene-ω-pentanor-15-[(3'-tert.butyl)-cyclopentyl]-prostacycl-5-en-13-ynoic acid;

(+)5Z-11α,15S-dihydroxy-9a-deoxy-9a-methylene-ω-pentanor-15-[(3'-vinyl)-cyclopentyl]-prostacycl-5-en-13-ynoic acid;

(+) 5Z-11α,15S-dihydroxy-9a-deoxy-9a-methylene-ω-pentanor-15-[(3'-isopropylidene)-cyclopentyl]-prostacycl-5-en-13-ynoic acid, N.M.R. (CDCl₃)δp.p.m: 1.70 (6H, s); 4.03 (1H, m); 4.22 (1H, broad d); 5.28 (1H, m).

(+)5Z-11α,15S-dihydroxy-9a-deoxy-9a-methylene-ω-pentanor-15-cyclohexyl-prostacycl-5-en-13-ynoic acid (0.12 g), NMR (CDCl₃) δp.p.m.: 5.27 (1H, t) H₅; 4.17 (1H, d) H₁₅; 4.00 (1H, m) H₁₁;

(+)5E-11α,15S-dihydroxy-9a-deoxy-9a-methylene-ω-pentanor-15-cyclohexyl-prostacycl-5-en-13-ynoic acid (0.18 g), NMR (CDCl₃)δp.p.m.: 5.26 (1H, t) H₅; 4.17 (1H, d) H₁₅; 4.01 (1H, m) H₁₁;

(+)5E-11α,15S-dihydroxy-9a-deoxy-9a-methylene-ω-pentanor-15-cyclobutyl-prostacycl-5-en-13-ynoic acid;

(+)5E-11α,15S-dihydroxy-9a-deoxy-9a-methylene-ω-pentanor-15-[(4'-methyl)-cyclohexyl]-prostacycl-5- en-13-ynoic acid, NMR (CDCl$_3$)δp.p.m.: 0.98 (3H, d); 3.99 (1H, m); 4.19 (1H, broad d); 5.25 (1H, m);

(+)5E-11α,15S-dihydroxy-9a-deoxy-9a-methylene-ω-pentanor-15-[(4'-ethyl)-cyclohexyl]-prostacycl-5-en-13-ynoic acid, NMR (CDCl$_3$)δp.p.m.: 0.91 (3H, d); 1.31 (2H, m); 3.95 (1H, m); 4.21 (1H, broad d); 5.27 (1H, m);

(+)5E-11α,15S-dihydroxy-9a-deoxy-9a-methylene-ω-pentanor-15-[(4'-tert.butyl)-cyclohexyl]-prostacycl-5-en-13-ynoic acid;

(+)5E-11α,15S-dihydroxy-9a-deoxy-9a-methylene-ω-pentanor-15-[(4'-vinyl)-cyclohexyl]-prostacycl-5-en-13-ynoic acid;

(30 )5E-11α,15S-dihydroxy-9a-deoxy-9a-methylene-ω-pentanor-15-[(4'-isopropylidene)-cyclohexyl]-prostacycl-5-en-13-ynoic acid, NMR (CDCl$_3$)δp.p.m.: 1.70 (6H, s); 4.01 (1H,m); 4.22 (1H, broad d); 5.27 (1H, m);

(+)5Z-11α, 15S-dihydroxy-9-a-deoxy-9a-methylene-ω-pentanor-15-cyclobutyl-prostacycl-5-en-13-ynoic acid;

(+)5Z-11α, 15S-dihydroxy-9a-deoxy-9a-methylene-107-pentanor-15-[(4'-methyl)-cyclohexyl]-prostacycl-5-en-13-ynoic acid, NMR (CDCl$_3$) δp.p.m: 0.98 (3H,d); 3.99 (1H,m); 4.19 (1H, broad d); 5.26 (1H,m);

(+) 5Z-11α, 15S-dihydroxy-9a-deoxy-9*a-methylene-ω-pentanor*-15-[(4'-ethyl)-cyclohexyl]-prostacycl-5-en-13-ynoic acid, NMR (CDCl$_3$)δp.p.m: 0.91 (3H,d); 1.31 (2H,m); 3.95 (1H,m); 4.21 (1H, broad d); 5.28 (1H,m);

(+)5Z-11α, 15S-dihydroxy-9a-methylene-ω-pentanor-15-[(4'-tert. butyl)-cyclohexy]-prostacycl-5-en-13-ynoic acid;

(+)5Z-11α, 15S-dihydroxy-9a-deoxy-9a-methylene-ω-pentanor-15-[(4'-vinyl)-cyclohexyl]-prostacycl-5-en-13-ynoic acid;

(+)5Z-11α, 15S-dihydroxy-9a-deoxy-9a-methylene-ω-pentanor-15-[(4'-isopropylidene)-cyclohexyl]-prostacycl-5-en-13-ynoic acid, NMR (CDCl$_3$) δp.p.m: 1.70 (6H,s); 4.01 (1H,m); 4.22 (1H, broad d); 5.28 (1H,m);

(+)5(Z,E)-11α, 15S-dihydroxy-9a-deoxy-9a-methylene-ω-pentanor-15-cyclobutyl-prostacycl-5-en-13-ynoic acid;

(+)5(Z,E)-11 α, 15S-dihydroxy-9a-deoxy-9a-methylene-ω-pentanor-15-[(4'-methyl)-cyclohexyl]-prostacycl-5-en-13-ynoic acid;

(+)5(Z,E)-11α, 15S-dihydroxy-9a-deoxy-9a-methylene-ω-pentanor-15-[(4'-ethyl)-cyclohexyl]-prostacycl-5-en-13-ynoic acid;

(+) 5(Z,E)-11α,15S-dihydroxy-9a-deoxy-9a-methylene-ω-pentanor-15-[(4'-tert.butyl)-cyclohexyl]-prostacycl-5-en-13-ynoic acid;

(+) 5(Z,E)-11α,15S-dihydroxy-9a-deoxy-9a-methylene-ω-pentanor-15-[(4'-vinyl)-cyclohexyl]-prostacycl-5-en-13-ynoic acid;

(+) 5 (Z,E)-11α, 15S-dihydroxy-9a-deoxy-9a-methylene-ω-pentanor-15-[(4'-isopropylidene)-cyclohexyl]-prostacycl-5-en-13-ynoic acid; and (+)5(Z,E)-11α, 15S-dihydroxy-9a-deoxy-9a-methylene-ω-pentanor-15-cyclohexyl-prostacycl-5-en-13-ynoic acid.

EXAMPLE 14

Dry potassium carbonate (0.26 g) was added to a solution of 5E-11α, 15S-dihydroxy-9-a-deoxy-9a-methylene-ω-pentanor-15-[(4'-vinyl)-cyclohexyl]-prostacycl-5-en-13-ynoic acid (0.5 g) and methyliodide (0.18 ml) in dry DMF (3.2 ml). The mixture was stirred at room temperature for 4 hours. The inorganic material was filtered, and the organic solution was diluted with water (20 ml) and exaustively extracted with diethyl ether. The ethereal extracts were collected, washed with water and evaporated affording the 5E-11α, 15S-dihydroxy-9a-deoxy-9a-methyleneω-pentanor-15-[(4'-vinyl)-cyclohexyl]-prostacycl-5-en-13-ynoic acid methyl ester. In analogous fashion the following methyl esters were obtained:

5E-11α, 15S-dihydroxy-9a-deoxy-9a-methylene-ω-pentanor-15-cyclohexyl]-prostacycl-5-en-13-ynoic acid methyl ester;

5E-11α, 15S-dihydroxy-9a-deoxy-9a-methylene-ω-pentanor-15-[(4'-methyl)-cyclohexyl]-prostacycl-5-en-13-ynoic acid methyl ester;

5E-11α, 15S-dihydroxy-9a-deoxy-9a-methylene-ω-pentanor-15-[(4'-ethyl)-cyclohexyl]-prostacycl-5-en-13-ynoic acid methyl ester;

5E-11α, 15S-dihydroxy-9a-deoxy-9a-methylene-ω-pentanor-15-[(4'-tert.butyl)-cyclohexyl]-prostacycl-5-en-13-ynoic acid methyl ester;

5E-11α, 15S-dihydroxy-9a-deoxy-9a-methylene-ω-pentanor-15-[(4'-isopropylidene)-cyclohexyl]-prostacycl-5-en-13-ynoic acid methyl ester;

5E-11α, 15S-dihydroxy-9a-deoxy-9a-methylene-ω-pentanor-15-cyclobutyl-prostacycl-5-en-13-ynoic acid methyl ester;

5Z-11α, 15S -dihydroxy-9a-deoxy-9a-methylene-ω-pentanor-15-cyclohexyl-prostacycl-5-en-13-ynoic acid methyl ester;

5Z-11α, 15S -dihydroxy-9a-deoxy-9a-methylene-ω-pentanor-15-[(4'-methyl)-cyclohexy]-prostacycl-5-en-13-ynoic acid methyl ester;

5Z-11α, 15S -dihydroxy-9a-deoxy-9a-methylene-ω-pentanor-15-[(4'-ethyl)-cyclohexyl]-prostacycl-5-en-13-ynoic acid methyl ester;

5Z-11α, 15S -dihydroxy-9a-deoxy-9a-methylene-ω-pentanor-15-[(4'-tert.butyl)-cyclohexyl]-prostacycl-5-en-13-ynoic acid methyl ester;

5Z-11α, 15S -dihydroxy-9a-deoxy-9a-methylene-ω-pentanor-15-[(4'-vinyl)-cyclohexyl]-prostacycl-5-en-13-ynoic acid methyl ester;

5Z-11α, 15S -dihydroxy-9a-deoxy-9a-methylene-ω-pentanor-15-[(4'-isopropylidene)-cyclohexyl]-prostacycl-5-en-13-ynoic acid methyl ester;

5Z-11α, 15S -dihydroxy-9a-deoxy-9a-methylene-ω-pentanor-15-cyclobutyl-prostacycl-5-en-13-ynoic acid methyl ester;

5(Z,E)-11α, 15S -dihydroxy-9a-deoxy-9a-methylene-ω-pentanor-15-cyclohexyl-prostacycl-5-en-13-ynoic acid methyl ester;

5(Z,E)-11α, 15S -dihydroxy-9a-deoxy-9a-methylene-ω-pentanor-15-[(4'-methyl)-cyclohexyl]-prostacycl-5-en-13-ynoic acid methyl ester;

5(Z,E)-11α, 15S -dihydroxy-9a-deoxy-9a-methylene-ω-pentanor-15-[(4'-methyl)-cyclohexyl]-prostacycl-5-en-13-ynoic acid methyl ester;

5(Z,E)-11α, 15S-dihydroxy-9a-deoxy-9a -methylene-ω-pentanor-15-[(4'-ethyl)-cyclohexyl]-prostacycl-5-en-13-ynoic acid methyl ester;

5(Z,E)-11α, 15S-dihydroxy-9a-deoxy-9a -methylene-ω-pentanor-15-[(4'-tert.butyl)-cyclohexyl]-prostacycl-5-en-13-ynoic acid methyl ester;

5(Z,E)-11α, 15S-dihydroxy-9a-deoxy-9a -methylene-ω-pentanor-15-[(4'-vinyl)-cyclohexyl]-prostacycl-5-en13-ynoic acid methyl ester;

5(Z,E)-11α, 15S-dihydroxy-9a-deoxy-9a -methylene-ω-pentanor-15-[(4'-isopropylidene)-cyclohexyl]-prostacycl-5-en-13-ynoic acid methyl ester; and 5(Z,E)-11α, 15S-dihydroxy-9a-deoxy-9a -methylene-ω-pentanor-15-cyclobutyl-prostacycl-5-en13-ynoic acid methyl ester.

EXAMPLE 15

Dry potassium carbonate (0.26 g) was added to a solution of 5E-11α, 15S-dihydroxy-9a-deoxy-9a-methylene-107 -pentanor-15-cyclopentyl-prostacycl-b 5-en-13-ynoic acid (0.48 g) and methyliodide (0.52 ml) in dry DMF (3.2 ml).

The mixture was stirred at room temperature for 4 hours. The organic material was filtered, and the organic solution was diluted with water (20 ml) and exaustively extracted with diethyl ester. The ethereal extracts were collected, washsed with water and evaporated affording the 5E-11α, 15S-dihydroxy-9a-deoxy-9a-methylene-ω-pentanor-15-cyclopentyl-prostacycl-5-en-13-ynoic acid methyl ester (0.41 g) NMR (CDCl$_3$) δp.p.m: 3.55 )(2H,broad m); 3.65 (3H,s); 3.93 (1H, broad m), 4.22 (1H, broad d); 5.22 (1H,m).

By analogous procedure the following methyl esters were obtained:

5E-11α, 15S-dihydroxy-9a-deoxy-9a-methylene-ω-pentanor-15-[(3'-methyl)-cyclopentyl]-prostacycl-5-en-13-ynoic acid methyl ester;

5E-11α, 15S-dihydroxy-9a-deoxy-9a-methylene-ω-pentanor-15-[(3'-ethyl)-cyclopentyl]-prostacycl-5-en-13-ynoic acid methyl ester;

5E-11α, 15S-dihydroxy-9a-deoxy-9a-methylene-ω-pentanor-15-[(3'-tert.butyl)-cyclopentyl]-prostacycl-5-en-13-ynoic acid methyl ester;

5E-11α, 15S-dihydroxy-9a-deoxy-9a-methylene-ω-pentanor-15-[(3'-vinyl)-cyclopentyl]-prostacycl-5-en-13-ynoic acid methyl ester;

5E-11α, 15S-dihydroxy-9a-deoxy-9a-methylene-ω-pentanor-15-[(3'-isopropylidene)-cyclopentyl]-prostacycl-5-en-13-ynoic acid methyl ester;

5Z-11α, 15S-dihydroxy-9a-deoxy-9a-methylene-ω-pentanor-15-cyclopentyl-prostacycl-5-en-13-ynoic acid methyl ester;

5Z-11α, 15S-dihydroxy-9a-deoxy-9a-methylene-ω-pentanor-15-[(3'-methyl)-cyclopentyl]-prostacycl-5-en-13-ynoic acid methyl ester;

5Z-11α, 15S-dihydroxy-9a-deoxy-9a-methylene-ω-pentanor-15-[(3'-ethyl)-cyclopentyl]-prostacycl-5-en-13-ynoic acid methyl ester;

5Z-11α, 15S-dihydroxy-9a-deoxy-9a-methylene-ω-pentanor-15-[(3'-tert.butyl)-cyclopentyl]-prostacycl-5-en-13-ynoic acid methyl ester;

5Z-11α, 15S-dihydroxy-9a-deoxy-9a-methylene-ω-pentanor-15-[(3'-vinyl)-cyclopentyl]-prostacycl-5-en-13-ynoic acid methyl ester;

5Z-11α, 15S-dihydroxy-9a-deoxy-9a-methylene-ω-pentanor-15-[(3'-isopropylidene)-cyclopentyl]-prostacycl-5-en-13-ynoic acid methyl ester;

5(Z,E)-11α, 15S-dihydroxy-9a-deoxy-9a-methylene-ω-pentanor-15-cyclopentyl-prostacycl-5-en-13-ynoic acid methyl ester;

5(Z,E)-11α, 15S-dihydroxy-9a-deoxy-9a-methylene-ω-pentanor-15-[(3'-methyl)-cyclopentyl]-prostacycl-5-en-13-ynoic acid methyl ester;

5(Z,E)-11α, 15S-dihydroxy-9a-deoxy-9a-methylene-ω-pentanor---[(3'-ethyl)-cyclopentyl]-prostacycl-5-en-13-ynoic acid methyl ester;

5(Z,E)-11α, 15S-dihydroxy-9a-deoxy-9a-methylene-ω-pentanor-15-[(3'-tert.butyl)-cyclopentyl]-prostacycl-5-en-13-ynoic acid methyl ester;

5(Z,E)-11α, 15S-dihydroxy-9a-deoxy-9a-methylene-ω-pentanor-15-[(3'-vinyl)-cyclopentyl]-prostacycl-5-en-13-unoic acid methyl ester; and 5(Z,E)-11α, 15S-dihydroxy-9a-deoxy-9a-methylene-ω-pentanor-15-[(3'-isopropylidene)-cyclopentyl]-prostacycl-5-en-13-ynoic acid methyl ester.

EXAMPLE 16

Dry potassium carbonate (0.26 g) was added to a solution of (+)5E-11α, 15S-dihydroxy-9a-deoxy-9a-methylene-ω-pentanor-15-cyclopentyl-prostacycl-5-en-13-ynoic acid (0.48 g) and methyliodide (0.52 ml) in dry DMF (3.2 ml).

The mixture was stirred at room temperature for 4 hours. The organic material was filtered, and the organic solution was diluted with water (20 ml) and exaustively extracted with diethyl ether. The ethereal extracts were collected, washed with water and evaporated affording the (+)5E-11α, 15S-dihydroxy-9a-deoxy-9a-methylene-ω-pentanor--15-cyclopentyl-prostacycl-5-en-13-ynoic acid methyl ester (0.41 g) NMR (CDCl$_3$) δp.p.m.: 3.55 (2H, broad m); 3.65 (3H, s); 3.93 (1H, broad m); 4.22 (1H, broad d); 5.22 (1H,m).

By analogous procedure the following methyl esters were obtained:

(+)5E-11α, 15S-dihydroxy-9a-deoxy-9a-methylene-ω-pentanor-15-[(3'-methyl)-cyclopentyl]-prostacycl-5-en-13-ynoic acid methyl ester;

(+)5E-11α, 15S-dihydroxy-9a-deoxy-9a-methylene-ω-pentanor-15-[(3'-ethyl)-cyclopentyl]-prostacycl-5-en-13-ynoic acid methyl ester;

(30)5E-11α, 15S-dihydroxy-9a-deoxy-9a-methylene-ω-pentanor-15-[(3'-tert.butyl)-cyclopentyl]-prostacycl-5-en-13-ynoic acid methyl ester;

(+) 5E-11α, 15S-dihydroxy-9a-deoxy-9a-methylene-ω-pentanor-15-[(3'-vinyl)-cyclopentyl]-prostacycl-5-en-13-ynoic acid methyl ester;

(+)5E-11α, 15S-dihydroxy-9a-deoxy-9a-methylene-ω-pentanor-15-[(3'-isopropylidene)-cyclopentyl]-prostacycl-5-en-13-ynoic acid methyl ester;

(+) 5Z-11α, 15S-dihydroxy-9a-deoxy9a-methylene-ω-pentanor-15-cyclopentyl-prostacycl-5-en-13-ynoic acid methyl ester;

(+) 5Z-11α, 15S-dihydroxy-9a-deoxy-9a-methylene-ω-pentanor-15-[(3'-methyl)-cyclopentyl]-prostacycl-5-en-13-ynoic acid methyl ester;

(+) 5Z-11α, 15S-dihydroxy-9a-deoxy-9a-methylene-ω-pentanor-15-[(3'-ethyl)-cyclopentyl]-prostacycl-5-en-13-ynoic acid methyl ester;

(+) 5Z-11α, 15S-dihydroxy-9a-deoxy-9a-methylene-ω-pentanor-15-[(3'-tert.butyl)-cyclopentyl]-prostacycl-5-en-13-ynoic acid methyl ester;

(+) 5Z-11α, 15S-dihydroxy-9a-deoxy-9a-methylene-ω-pentanor-15-[(3'-vinyl)-cyclopentyl]-prostacycl-5-en-13-ynoic acid methyl ester;

(+) 5Z-11α, 15S-dihydroxy-9a-deoxy-9a-methylene-ω-pentanor-15-[(3'-isopropylidene)-cyclopentyl]-prostacycl-5-en-13-ynoic acid methyl ester;

(+) 5(Z,E)-11α,15S-dihydroxy-9a-deoxy9a-methylene-ω-pentanor-15-cyclopentyl-prostacycl-5-en-13-ynoic acid methyl ester;

(+)5(Z,E)-11α,15S-dihydroxy-9a-deoxy-9a-methylene-ω-pentanor-15-[(3'-methyl)-cyclopentyl]-prostacycl-5-en-13-ynoic acid methyl ester;

(+)5(Z,E)-11α,15S-dihydroxy-9a-deoxy-9a-methylene-ω-pentanor-15-[(3'-ethyl)-cyclopentyl]-prostacycl-5-en-13-ynoic acid methyl ester;

(+)5(Z,E)-11α,15S-dihydroxy-9a-deoxy-9a-methylene-ω-pentanor-15-[(3'-tert.butyl)-cyclopentyl]-prostacycl-5-en-13-ynoic acid methyl ester;

(+)5(Z,E)-11α,15S-dihydroxy-9a-deoxy-9a-methylene-ω-pentanor-15-[(3'-vinyl)-cyclopentyl]-prostacycl-5-en-13-ynoic acid methyl ester;

(+)5(Z,E)-11α,15S-dihydroxy-9a-deoxy-9a-methylene-ω-pentanor-15-[(3'-isopropylidene)-cyclopentyl]-prostacycl-5-en-13-ynoic acid methyl ester;

(+)5E-11α,15S-dihydroxy-9a-deoxy-9a-methylene-ω-pentanor-15-cyclohexyl-prostacycl-5-en-13-ynoic acid methyl ester;

(+)5E-11α,15S-dihydroxy-9a-deoxy-9a-methylene-ω-pentanor-15-[(4'-methyl)-cyclohexyl]-prostacycl-5-en-13-ynoic acid methyl ester;

(+)5E-11α,15S-dihydroxy-9a-deoxy-9a-methylene-ω-pentanor-15-[(4'-ethyl)-cyclohexyl-]-prostacycl-5-en-13-ynoic acid methyl ester;

(+)5E-11α,15S-dihydroxy-9a-deoxy-9a-methylene-ω-pentanor-15-[(4'-tert.butyl)-cyclohexyl]-prostacycl-5-en-13-ynoic acid methyl ester;

(+)5E-11α,15S-dihydroxy-9a-deoxy-9a-methylene-ω-pentanor-15-[(4'-vinyl)-cyclohexyl]-prostacycl-5-en-13-ynoic acid methyl ester;

(+)5E-11α,15S-dihyroxy-9a-deoxy-9a-methylene-ω-pentanor-15-[(4'-isopropylidene)-cyclohexyl]-prostacycl-5-en-13-ynoic acid methyl ester;

(+)5E-11α,15S-dihydroxy-9a-deoxy-9a-methylene-ω-pentanor-15-cyclobutyl-prostacycl-5-en-13-ynoic acid methyl ester;

(+)5Z-11α,15S-dihydroxy-9a-deoxy-9a-methylene-ω-pentanor-15-cyclohexyl-prostacycl-5-en-13-ynoic acid methyl ester;

(30 )5-Z-11α,15S-dihydroxy-9a-deoxy-9a-methylene-ω-pentanor-15-[(4'-methyl)-cyclohexyl]-prostacycl-5-en-13-ynoic acid methyl ester;

(+)5Z-11α,15S-dihydroxy-9a-deoxy-9a-methylene-ω-pentanor-15-[(4'-ethyl)-cyclohexyl]-prostacycl-5-en-13-ynoic acid methyl ester;

(+)5Z-11α,15S-dihydroxy-9a-deoxy-9a-methylene-ω-pentanor-15-[(4'-tert.butyl)-cyclohexyl]-prostacycl-5-en-13-ynoic acid methyl ester;

(30)5Z-11α,15S-dihydroxy-9a-deoxy-9a-methylene-ω-pentanor-15-[(4'-vinyl)-cyclohexyl]-prostacycl-5-en-13-ynoic acid methyl ester;

(+)5Z-11α,15S-dihydroxy-9a-deoxy-9a-methylene-ω-pentanor-15-[(4'-isopropylidene)-cyclohexyl]-prostacycl-5-en-13-ynoic acid methyl ester;

(+)5Z-11α,15S-dihydroxy-9a-deoxy-9a-methylene-ω-pentanor-15-cyclobutyl-prostacycl-5-en-13-ynoic acid methyl ester;

(+)5Z,E-11α,15S-dihydroxy-9a-deoxy-9a-methylene-ω-pentanor-15-cyclohexyl-prostacycl-5-en-13-ynoic acid methyl ester;

(+) 5(Z,E)-11α,15S-dihydroxy-9a-deoxy-9a-methylene-ω-pentanor-15-[(4'-methyl)-cyclohexyl]-prostacycl-5en-13-ynoic acid methyl ester;

(+)5(Z,E)-11α,15S-dihydroxy-9a-deoxy-9a-methylene-ω-pentanor-15-[(4'-ethyl)-cyclohexyl-]-prostacycl-5-en-13-ynoic acid methyl ester;

(+)5(Z,E)-11α,15S-dihydroxy-9a-deoxy-9a-methylene-ω-pentanor-15-[(4'-tert.butyl)-cyclohexyl]-prostacycl-5-en-13-ynoic acid methyl ester;

(+)5(Z,E)-11α,15S-dihydroxy-9a-deoxy-9a-methylene-ω-pentanor-15-[(4'-vinyl)-cyclohexyl]-prostacycl-5-en-13-ynoic acid methyl ester;

(+)5(Z,E)-11α,15S-dihydroxy-9a-deoxy-9a -methylene-ω-pentanor-15-[(4'-isopropylidene)-cyclohexyl]-prostacycl-5-en-13- ynoic acid methyl ester; and (+)5(Z,E)-11α,15S-dihydroxy-9a-deoxy-9a-methylene-ω-pentanor-15-cyclobutyl-prostacycl-5-en-13-ynoic acid methyl ester.

EXAMPLE 17

A solution of 5E-11α,15S-dihydroxy-9a-deoxy-9a-methylene-ω-pentanor-15-cyclohexyl-prostacycl-5-en-13-ynoic acid (0.2 g) in THF (3 ml) was treated with 0.25 g of 0-β(piperidinoethyl)-dicyclohexyl-iso-urea for 15 hours at reflux temperature. The solvent was evaporated in the vacuo and the residue was partitioned between diethyl ether and 5% aqueous-NaHCO$_3$.

The organic phase was separated, washed with water dried and evaporated to dryness. Chromatographic purification on SiO$_2$ gel [eluent: CHCl$_3$ (90); MeOH (10); NH$_4$OH (0.1)]afforded 5E-11α,15S-dihydroxy-9a-deoxy-9a-methylene-ω-pentanor-15-cyclohexyl-prostacycl-5-en-13-ynoic acid-β-piperidino ethyl ester;

By analogous procedure the following compounds were obtained:

5E-11α,15S-dihydroxy-9a-deoxy-9a-methylene-ω-pentanor-15-[(4'-methyl)-cyclohexyl]-prostacycl-5-en-13-ynoic acid-β-piperidino ethyl ester;

5E-11α,15S-dihydroxy-9a-deoxy-9a-methylene-ω-pentanor-15-[(4'-ethyl)-cyclohexyl]-prostacycl-5-en-13-ynoic acid-β-piperidino ethyl ester;

5E-11α,15S-dihydroxy-9a-deoxy-9a-methylene-ω-pentanor-15-[(4'-tert.butyl)-cyclohexyl]-prostacycl-5-en-13-ynoic acid -β-piperidino ethyl ester;

5E-11α,15S-dihydroxy-9a-deoxy-9a-methylene-ω-pentanor-15-[(4'-vinyl)-cyclohexyl]-prostacycl-5-en-13-ynoic acid -β-piperidino ethyl ester;

5E-11α,15S-dihydroxy-9a-deoxy-9a-methylene-ω-pentanor-15-[(4'-isopropylidene)-cyclohexyl]-prostacycl-5-en-13-ynoic acid-β-piperidino ethyl ester;

5E-11α,15S-dihydroxy-9a-deoxy-9a-methylene-ω-pentanor-15-cyclopentyl-prostacycl-5-en-13-ynoic acid-β-piperidino ethyl ester;

5E-11α,15S-dihydroxy-9a-deoxy-9a-methylene-ω-pentanor-15-[(3'-methyl)-cyclopentyl]-prostacycl-5-en-13-ynoic acid-β-piperidino ethyl ester;

5E-11α,15S-dihydroxy-9a-deoxy-9a-methylene-ω-pentanor-15-[(3'-ethyl)-cyclopentyl]-prostacycl-5-en-13-ynoic acid-β-piperidino ethyl ester;

5E-11α,15S-dihydroxy-9a-deoxy-9a-methylene-ω-pentanor-15-[(3'-isopropylidene)-cyclopentyl]-prostacycl-5-en-13-ynoic acid-β-piperidino ethyl ester;

5E-11α,15S-dihydroxy-9a-deoxy-9a-methylene-ω-pentanor-15-cyclobutyl-prostacycl-5-en-13-ynoic acid-β-piperidino ethyl ester;

5Z-11α,15S-dihydroxy-9a-deoxy-9a-methylene-ω-pentanor-15-cyclohexyl-prostacycl-5-en-13-ynoic acid-β-piperidino ethyl ester;

5Z-11α,15S-dihydroxy-9a-deoxy-9a-methylene-ω-pentanor-15-[(4'-methyl)-cyclohexyl]-prostacycl-5-en-13-ynoic acid-β-piperidino ethyl ester;

5Z-11α,15S-dihydroxy-9a-deoxy-9a-methylene-ω-pentanor-15-[(4'-ethyl)-cyclohexyl]-prostacycl-5-en-13ynoic acid-β-piperidino ethyl ester;

5Z-11α,15S-dihydroxy-9a-deoxy-9a-methylene-ω-pentanor-15-[(4'-tert.butyl)-cyclohexyl]-prostacycl-5-en-13-ynoic acid-β-piperidino ethyl ester;

5Z-11α,15S-dihydroxy-9a-deoxy-9a-methylene-ω-pentanor-15-[(4'-vinyl)-cyclohexyl]-prostacycl-5-en-13-ynoic acid-β-piperidino ethyl ester;

5Z-11α,15S-dihydroxy-9a-deoxy-9a-methylene-ω-pentanor-15-[(4'-isopropylidene)-cyclohexyl]-prostacycl-5-en-13-ynoic acid-β-piperidino ethyl ester;

5Z-11α,15S-dihydroxy-9a-deoxy-9a-methylene-ω-pentanor-15-cyclopentyl-prostacycl-5-en-13-ynoic acid-β-piperidinoethyl ester;

5Z-11α,15S-dihydroxy-9a-deoxy-9a-methylene-ω-pentanor-15-[(3'-methyl)-cyclopentyl]-prostacycl-5-en-13-ynoic acid-β-piperidino ethyl ester;

5Z-11α,15S-dihydroxy-9a-deoxy-9a-methylene-ω-pentanor-15-[(3'-ethyl)-cyclopentyl]-prostacycl-5-en-13-ynoic acid-β-piperidino ethyl ester;

5Z-11α,15S-dihydeoxy-9a-deoxy-9a-methylene-ω-pentanor-15-[(3'-isopropylidene)-cyclopentyl]-prostacycl-5-en-13-ynoic acid-β-piperidino ethyl ester;

5Z-11α,15S-dihydroxy-9a-deoxy-9a-methylene-ω-pentanor-15-cyclobutyl-prostacycl-5-en-13-ynoic acid-β-piperidino ethyl ester;

5(Z,E)-11α,15S-dihydroxy-9a-deoxy-9a-methylene-ω-pentanor-15-cyclohexyl-prostacycl-5-en-13-ynoic acid-β-piperidino ethyl ester;

5(Z,E)-11α,15S-dihydroxy-9a-deoxy-9a-methylene-ω-pentanor-15-[(4'-methyl)-cyclohexyl]-prostacycl-5-en-13-ynoic acid-β-piperidino ethyl ester;

5(Z,E)-11α,15S-dihydroxy-9a-deoxy-9a-methylene-ω-pentanor-15-[(4'-ethyl)-cyclohexyl]-prostacycl-5-en-13-ynoic acid -β-piperidino ethyl etster;

5(Z,E)-11α,15S-dihydroxy-9a-deoxy-9a-methylene-ω-pentanor-15-[(4'-tert.butyl)-cyclohexyl]-prostacycl-5-en-13-ynoic acid-62-piperidino ethyl ester;

5(Z,E)-11α,15S-dihydroxy-9a-deoxy-9a-methylene-ω-pentanor-15-[(4'-vinyl)-cyclohexyl]-prostacycl-5-en-13-ynoic acid-β-piperidino ethyl ester;

5(Z,E)-11α,15S-dihydroxy-9a-deoxy-9a-methylene-ω-pentanor-15-[(4'-isopropylidene)-cyclohexyl]-prostacycl-5-en-13-ynoic acid-β-piperidino ethyl ester;

5(Z,E)-11α,15S-dihydroxy-9a-deoxy-9a-methylene-ω-pentanor-15-cyclopentyl-prostacycl-5-en-13-ynoic acid-β-piperidino ethyl ester;

5(Z,E)-11α,15S-dihydroxy-9a-deoxy-9a-methylene-ω-pentanor-15-[(3'-methyl)-cyclopentyl]-prostacycl-5-en-13-ynoic acid-β-piperidino ethyl ester;

5(Z,E)-11α,15S-dihydroxy-9a-deoxy-9a-methylene-ω-pentanor-15-[(3'-ethyl)-cyclopentyl]-prostacycl-5-en-13-ynoic acid-β-piperidino ethyl ester;

5(Z,E)-11α,15S-dihydroxy-9a-deoxy-9a-methylene-ω-pentanor-15-[(3'-isopropylidene)-cyclopentyl]-prostacycl-5-en-13-ynoic acid-β-piperidino ethyl ester;

5(Z,E)-11α,15S-dihydroxy-9a-deoxy-9-methylene-ω-pentanor-15-cyclobutyl-prostacycl-5-en-13-ynoic acid-β-piperidino ethyl ester, and the (+) enantiomers of all the hereabove listed compounds.

EXAMPLE 18

Using in the procedure of the example 17 O-β(morpholino-ethyl)-dicyclohexyl-iso-urea.

5E-11α, 15S-dihydroxy-9a-deoxy-9a-methylene-ω-pentanor-15-cyclohexyl-prostacycl-5-en-13-ynoic acid-β-morpholino-ethyl ester was obtained.

In analoguous fashion the following compounds were prepared:

5E-11α, 15S-dihydroxy-9a-deoxy-9a-methylene-ω-pentanor-15-[(4'-methyl)-cyclohexyl]-prostacycl-5-en-13-ynoic acid -β-morpholino ethyl ester;

5E-11α, 15S-dihydroxy-9a-deoxy-9a-methylene-ω-pentanor-15-[(4'-ethyl)-cyclohexyl]-prostacycl-5-en-13-ynoic acid-β-morpholino ethyl ester;

5E-11α, 15S-dihydroxy-9a-deoxy-9a-methylene-ω-pentanor-15-[(4'-tert.butyl)-cyclohexyl]-prostacycl-5-en-13-ynoic acid-β-morpholino ethyl ester;

5E-11α, 15S-dihydroxy-9a-deoxy-9a-methylene-ω-pentanor-15-[(4'-vinyl)-cyclohexyl]-prostacycl-5-en-13-ynoic acid-βmorpholino ethyl ester;

5E-11α, 15S-dihydroxy-9a-deoxy-9a-methylene-ω-pentanor-15-[(4'-isopropylidene)-cyclohexyl]-prostacycl-5-en-13-ynoic acid-βmorpholino ethyl ester;

5E-11α, 15S-dihydroxy-9a-deoxy-9a-methylene-ω-pentanor-15-cyclopentyl-prostacycl-5-en-13-ynoic acid-βmorpholino ethyl ester;

5E-11α, 15S-dihydroxy-9a-deoxy-9a-methylene-ω-pentanor-15-[(3'-methyl)-cyclopentyl]prostacycl-5-en-13-ynoic acid-βmorpholino ethyl ester;

5E-11α, 15S-dihydroxy-9a-deoxy-9a-methylene-ω-pentanor-15-[(3'-ethyl)-cyclopentyl]-prostacycl-5-en-13-ynoic acid-β-morpholino ethyl ester;

5E11α, 15S-dihydroxy-9a-deoxy-9a-methylene-ω-pentanor-15-[(3'-isopropylidene)-cyclopentyl]-prostacycl-5-en-13-ynoic acid-β-morpholino ethyl ester;

5E-11α, 15S-dihydroxy-9a-deoxy-9a-methylene-ω-pentanor-15-cyclobutyl-prostacycl-5-en-13-ynoic acid-βmorpholino ethyl ester;

5Z-11α, 15S-dihydroxy-9a-deoxy-9a-methylene-ω-pentanor-15-cyclohexyl-prostacycl-5-en-13-ynoic acid-βmorpholino ethyl ester;

5Z-11α, 15S-dihydroxy-9a-deoxy-9a-methylene-ω-pentanor-15-[(4'-methyl)-cyclohexyl]-prostacycl-5-en-13-ynoic acid-βmorpholino ethyl ester;

5Z-11α, 15S-dihydroxy-9a-deoxy-9a-methylene-ω-pentanor-15-[(4'-ethyl)-cyclohexyl]-prostacycl-5-en-13-ynoic acid-βmorpholino ethyl ester;

5Z-11α, 15S-dihydroxy-9a-deoxy-9a-methylene-107-pentanor-15-[(4'-tert.butyl)-cyclohexyl]-prostacycl-5-en-13-ynoic acid-β-morpholino ethyl ester;

5Z-11α, 15S-dihydroxy-9a-deoxy-9a-methylene-107-pentanor-15-[(4'-vinyl)-cyclohexyl]-prostacycl-5-en-13-ynoic acid-β-morpholino ethyl ester;

5Z-11α, 15S-dihydroxy-9a-deoxy-9a-methylene-107-pentanor-15-[(4'-isopropylidene)-cyclohexyl]-prostacycl-5-en-13-ynoic acid-β-morpholino ethyl ester;

5Z-11α, 15S-dihydroxy-9a-deoxy-9a-methylene-107-pentanor-15-cyclopentyl-prostacycl-5-en-13-ynoic acid-β-morpholino ethyl ester;

5Z-11α, 15S-dihydroxy-9a-deoxy-9a -methylene-ω-pentanor-15-[(3'-methyl)-cyclopentyl]-prostacycl-5-en-13-ynoic acid-β-morpholino ethyl ester;

5Z-11α, 15S-dihydroxy-9a-deoxy-9a -methylene-ω-pentanor-15-[(3'-ethyl)-cyclopentyl]-prostacycl-5-en-13-ynoic acid-β-morpholino ethyl ester;

5Z-11α, 15S-dihydroxy-9a-deoxy-9a -methylene-ω-pentanor-15-[(3'-isopropylidene)-cyclopentyl]-prostacycl-5-en-13-ynoic acid-β-morpholino ethyl ester;

5Z-11α, 15S-dihydroxy-9a-deoxy-9a -methylene-ω-pentanor-15-cyclobutyl-prostacycl-5-en-13-ynoic acid-β-morpholino ethyl ester;

5(Z,E)-11α, 15S-dihydroxy-9a-deoxy-9a -methylene-ω-pentanor-15-cyclohexyl-prostacycl-5-en-13-ynoic acid-β-morpholino ethyl ester;

5(Z,E)-11α, 15S-dihydroxy-9a-deoxy9a-methylene-ω-pentanor-15-[(4'-methyl)-cyclohexyl]-prostacycl-5-en-13-ynoic acid-β-morpholino ethyl ester;

5(Z,E)-11α, 15S-dihydroxyy-9a-deoxy-9a-methylene-ω-pentanor-15-[(4'-ethyl)-cyclohexyl]-prostacycl-5-en-13-ynoic acid-β-morpholino ethyl ester;

5(Z,E)-11α, 15S-dihydroxy-9a-deoxy-9a-methylene-ω-pentanor-15-[(4'-tert.butyl)-cyclohexyl]-prostacyclo-5-en-13-ynoic acid-β2-morpholino ethyl ester;

5(Z,E)-11α, 15S-dihydroxy-9a-deoxy-9a-methylene-ω-pentanor-15-[(4'-vinyl)-cyclohexyl]prostacycl-5-en-13-ynoic acid-β-morpholino ethyl ester;

5(Z,E)-11α, 15S-dihydroxy-9a-deoxy-9a-*methylene-ωpentanor*-15-[(4'-isopropylidene)-cyclohexyl]-prostacycl-5-en-13-ynoic acid-β-morpholic ethyl ester;

5(Z,E)-11α, 15S-dihydroxy-9a-deoxy-9a-methylene-ω-pentanor-15-cyclopentyl-prostacycl-5-en-13-ynoic acid-β-morpholino ethyl ester;

5(Z,E)-11α, 15S-dihydroxy-9a-deoxy-9a-methylene-ω-pentonor-15-[(3'-methyl)-cyclopentyl]-prostacycl-5-en-13-ynoic acid-β-morpholino ethyl ester;

5(Z,E)-11α-15S-dihydroxy-9a-deoxy-9a-methylene-ω-pentanor-15-[(3'-ethyl)-cyclopentyl]-prostacycl-5-en-13-ynoic acid-β-morpholino ethyl ester;

5(Z,E)-11α,15S-dihydroxy-9a-deoxy-9a-methylene-ω-pentanor-15-[(3'-isopropylidene)-cyclopentyl]-prostacycl-5-en-13-ynoic acid-β-morpholino ethyl ester;

5(Z,E)-11,α15S-dihydroxy-9a-deoxy-9a-methylene-ω-pentanor-15-cyclobutyl-prostacycl-5-en-13-ynoic acid-β-morpholino ethyl ester, and the (+) enantiomers of all the hereabove listed compounds.

EXAMPLE 19

Using in the procedure of the examples 11 and 13 3-carboxy-propyltriphenylphosphonium bromide, 5-carboxy-n-pentyl-triphenylphosphonium bromide and 6-carboxy-n-hexyl-triphenylphosphonium bromide, instead of 4-carboxy-butyl-triphenylphosphonium bromide, the following compounds were, respectively, obtained:

5E-11α, 15S-dihydroxy-9a-deoxy-9a-methylene-2-nor-ω-pentanor-15-cyclohexyl-prostacycl-5-en-13-ynoic acid;

5Z-11α, 15S-dihydroxy-9a-deoxy-9a-methylene2-nor-ω-pentanor-15-cyclohexyl-prostacycl-5-en-13-ynoic acid;

5E-11α, 15S-dihydroxy-9a-deoxy-9a-methylene2a-homo-ω-pentanor-15-cyclohexyl-prostacycl5-en-13-ynoic acid;

5Z-11α, 15S-dihydroxy-9a-deoxy-9a-methylene-2a-homo-ω-pentanor-15-cyclohexyl-prostacycl-5-en-13-ynoic acid;

5E-11α, 15S-dihydroxy-9a-deoxy-9a-methylene-2a,2b-dihomo-ω-pentanor-15-cyclohexyl-prostacycl-5-en-13-ynoic acid; and 5Z-11α, 15S-dihydroxy-9a-deoxy-9a-methylene-2a,2b-dihomo-ω-pentanor-15-cyclohexyl-prostacycl-5-en-13-ynoic acid.

By analogous procedure, using the above indicated phosponium bromides and the appropriate bicyclo [3.3.0]octane derivatives the following compounds were prepared too:

5E-11α, 15S-dihydroxy-9a-deoxy-9a-methylene-2-nor-ω-pentanor-15-[(4'-methyl)-cyclohexyl]-prostacycl-5-en-13-ynoic acid;

5E-11α, 15S-dihydroxy-9a-deoxy-9a-methylene-2-nor-ω-pentanor-15-[(4'-ethyl)-cyclohexyl]-prostacycl-5-en-13-ynoic acid;

5E-11α, 15S-dihydroxy-9a-deoxy-9a-methylene2-nor-ω-pentanor-15-[(4'-tert.butyl)-cyclohexyl]-prostacycl-5-en-13-ynoic acid;

5E-11α, 15S-dihydroxy-9a-deoxy-9a-methylene2-nor-ω-pentanor-15-[(4'-vinyl)-cyclohexyl]-prostacycl-5-en-13-ynoic acid;

5E-11α, 15S-dihydroxy-9a-deoxy-9a-methylene2-nor-ω-pentanor-15-[(4'-isopropylidene)-cyclohexyl]-prostacycl-5-en-13-ynoic acid;

5E-11α, 15S-dihydroxy-9a-deoxy-9a-methylene-2-nor-ω-pentanor-15-cyclopentyl-prostacycl-5-en-13-ynoic acid;

5E-11α, 15S-dihydroxy-9a-deoxy-9a-methylene2-nor-ω-pentanor-15-[(3'-methyl)-cyclopentyl-prostacycl-5-en-13-ynoic acid;

5E-11α, 15S-dihydroxy-9a-deoxy-9a-methylene-2-nor-ω-pentanor-15-[(3'-ethyl)-cyclopentyl]-prostacycl-5-en-13-ynoic acid;

5E-11α, 15S-dihydroxy-9a-deoxy-9a-methylene-2-nor-ω-pentanor-15-[(3'-isopropylidene)-cyclopentyl-prostacycl-5-en-13-ynoic acid;

5E-11α, 15S-dihydroxy-9a-deoxy-9a-methylene-2-nor-ω-pentanor-15-cyclobutyl-prostacycl-5-en-13-ynoic acid;

5E-11α, 15S-dihydroxy-9a-deoxy-9a-methylene-2-nor-ω-pentanor-15-[(4'-methyl)-cyclohexyl]-prostacycl-5-en-13-ynoic acid;

5E-11α, 15S-dihydroxy-9a-deoxy-9a-methylene-2a-homo-ω-pentanor-15-[(4'-ethyl)-cyclohexyl]prostacycl-5-en-13-ynoic acid;

5E-11α,15S-dihydroxy-9a-deoxy-9a-methylene-2a-homo-ω-pentanor-15-[(4'-tert.butyl)-cyclohexyl]-prostacycl-5-en-13-ynoic acid;

5E-11α,15S-dihydroxy-9a-deoxy-9a-methylene-2a-homo-ω-pentanor-15-[(4'-vinyl)-cyclohexyl]-prostacycl-5-en-13-ynoic acid;

5E-11α,15S-dihydroxy-9a-deoxy-9a-methylene-2a-homo-ω-pentanor-15-[(4'-isopropylidene)-cyclohexyl]-prostacycl-5-en-13-ynoic acid;

5E-11α,15S-dihydroxy-9a-deoxy-9a-methylene-2a-homo-ω-pentanor-15-cyclopentyl-prostacycl-5-en-13ynoic acid;

5E-11α,15S-dihydroxy-9a-deoxy-9a-methylene-2a-homo-ω-pentanor-15-[(3'-methyl)-cyclopentyl]-prostacycl-5-en-13-ynoic acid;

5E-11α,15S-dihydroxy-9a-deoxy-9a-methylene-2a-homo-ω-pentanor-15-[(3'-ethyl)-cyclopentyl]-prostacycl-5-en-13-ynoic acid;

5E-11α,15S-dihydroxy-9a-deoxy-9a-methylene-2a-homo-ω-pentanor-15-[(3'isopropylidene)-cyclopentyl]-prostacycl-5-en-13-ynoic acid;

5E-11α,15S-dihydroxy-9a-deoxy-9a-methylene-2a-homo-ω-pentanor-15-cyclobutyl-prostacycl-5-en-13-ynoic acid;

5E-11α,15S-dihydroxy-9a-deoxy-9a-methylene-2a,2b-dihomo-ω-pentanor-15-[(4'-methyl)-cyclohexyl]-prostacycl-5-en-13-ynoic acid;

5E-11α,15S-dihydroxy-9a-deoxy-9a-methylene-2a,2b-dihomo-ω-pentanor-15-[(4'-ethyl)-cyclohexy]-prostacycl-5-en-13-ynoic acid;

5E-11α,15S-dihydroxy-9a-deoxy-9a-methylene-2a,2b-dihomo-ω-pentanor-15-[(4'-tert.butyl)-cyclohexyl]-prostacycl-5-en-13-ynoic acid;

5E-11α,15S-dihydroxy-9a-deoxy-9a-methylene-2a,2b-dihomo-ω-pentanor-15-[(4'-vinyl)-cyclohexyl]-prostacycl-5-en-13-ynoic-acid;

5E-11α,15S-dihydroxy-9a-deoxy-9a-methylene-2a,2b-dihomo-ω-pentanor-15-[(4'-isopropylidene)-cyclohexyl]-prostacycl-5-en-13-ynoic acid;

5E-11α,15S-dihydroxy-9a-deoxy-9a-methylene-2a,2b-dihomo-ω-pentanor-15-cyclopentyl-prostacycl-5-en-13-ynoic acid;

5E-11α,15S-dihydroxy-9a-deoxy-9a-methylene-2a,2b-dihomo-ω-pentanor-15-[(3'-methyl)-cyclopentyl]-prostacycl-5-en-13-ynoic acid;

5E-11α,15S-dihydroxy-9a-deoxy-9a-methylene-2a,2b-dihomo-ω-pentanor-15-[(3'-ethyl)-cyclopentyl]-prostacycl-5-en-13-ynoic acid;

5E-11α,15S-dihydroxy-9a-deoxy-9a-methylene-2a,2b-dihomo-ω-pentanor-15-[(3'-isopropylidene)-cyclopentyl]-prostacycl-5-en-13-ynoic acid;

5E-11α,15S-dihydroxy-9a-deoxy-9a-methylene-2a,2b-dihomo-ω-pentanor-15-cyclobutyl-prostacycl-5-en-13-ynoic acid;

5Z-11α,15S-dihydroxy-9a-deoxy-9a-methylene-2-nor-ω-pentanor-15-[(4'-methyl)-cyclohexyl]-prostacycl-5-en-13-ynoic acid;

5Z-11α,15S-dihydroxy-9a-deoxy-9a-methylene-2-nor-ω-pentanor-15-[(4'-ethyl)-cyclohexyl]-prostacycl-5-en-13-ynoic acid;

5Z-11α,15S-dihydroxy-9a-deoxy-9a-methylene-2-nor-ω-pentanor-15-[(4'-tert.butyl)-cyclohexyl]-prostacycl-5-en-13-ynoic acid;

5Z-11α,15S-dihydroxy-9a-deoxy-9a-methylene-2-nor-ω-pentanor-15-[(4'-vinyl)-cyclohexyl]-prostacycl-5-en-13-ynoic acid;

5Z-11α,15S-dihydroxy-9a-deoxy-9a-methylene-2-nor-ω-pentanor-15-[(4'-isopropylidene)-cyclohexyl]-prostacycl-5-en-13-ynoic acid;

5Z-11α,15S-dihydroxy-9a-deoxy-9a-methylene-2-nor-ω-pentanor-15-cyclopentyl-prostacycl-5-en-13-ynoic acid;

5Z-11α,15S-dihydroxy-9a-deoxy-9a-methylene-2-nor-ω-pentanor-15-[(3'-methyl)-cyclopentyl]-prostacycl-5-en-13-ynoic acid;

5Z-11α,15S-dihydroxy-9a-deoxy-9a-methylene-2-nor-ω-pentanor-15-[(3'-ethyl)-cyclopentyl]-prostacycl-5-en-13-ynoic acid;

5Z-11α,15S-dihydroxy-9a-deoxy-9a-methylene-2-nor-ω-pentanor-15-[(3'-isopropylidene)-cyclopentyl]-prostacycl-5-en-13-ynoic acid;

5Z-11α,15S-dihydroxy-9a-deoxy-9a-methylene-2-nor-ω-pentanor-15-cyclobutyl-prostacycl-5-en-13-ynoic acid;

5Z-11α,15S-dihydroxy-9a-deoxy-9a-methylene-2a-homo-ω-pentanor-15-[(4'-methyl)-cyclohexyl]-prostacycl-5-en-13-ynoic acid;

5Z-11α,15S-dihydroxy-9a-deoxy-9a-methylene-2a-homo-ω-pentanor-15-[(4'-ethyl)-cyclohexyl]-prostacycl-5-en-13-ynoic acid;

5Z-11α,15S-dihydroxy-9a-deoxy-9a-methylene-2a-homo-ω-pentanor-15-[(4'-tert.butyl)-cyclohexyl]-prostacycl-5-en-13-ynoic acid;

5Z-11α,15S-dihydroxy-9a-deoxy-9a-methylene-2a-homo-ω-pentanor-15-[(4'-vinyl)-cyclohexyl]-prostacycl-5-en-13-ynoic acid;

5Z-11α,15S-dihydroxy-9a-deoxy-9a-methylene-2a-homo-ω-pentanor-15-[(4'-isopropylidene)-cyclohexyl]-prostacycl-5-en-13-ynoic acid;

5Z-11α,15S-dihydroxy-9a-deoxy-9a-methylene-2a-homo-ω-pentanor-15-cyclopentyl-prostacycl-5-en-13-ynoic acid;

5Z-11α,15S-dihydroxy-9a-deoxy-9a-methylene-2a-homo-ω-pentanor-15-[(3'-methyl)-cyclopentyl]-prostacycl-5-en-13-ynoic acid;

5Z-11α,15S-dihydroxy-9a-deoxy-9a-methylene-2a-homo-ω-pentanor-15-[(3'-ethyl)-cyclopentyl]-prostacycl-5-en-13-ynoic acid;

5Z-11α,15S-dihydroxy-9a-deoxy-9a-methylene-2a-homo-ω-pentanor-15-[(3'-isopropylidene)-cyclopentyl]-prostacycl-5-en-13-ynoic acid;

5Z-11α,15S-dihydroxy-9a-deoxy-9a-methylene-2a-homo-ω-pentanor-15-cyclobutyl-prostacycl-5-en-13-ynoic acid;

5Z-11α,15S-dihydroxy-9a-deoxy-9a-methylene-2a,2b-dihomo-ω-pentanor-15-[(4'-methyl)-cyclohexyl]-prostacycl-5-en-13-ynoic acid;

5Z-11α,15S-dihydroxy-9a-deoxy-9a-methylene-2a,2b-dihomo-ω-pentanor-15-[(4'-ethyl)-cyclohexyl]-prostacycl-5-en-13-ynoic acid;

5Z-11α,15S-dihydroxy-9a-deoxy-9a-methylene-2a,2b-dihomo-ω-pentanor-15-[(4'-tert.butyl)-cyclohexyl]-prostacycl-5-en-13-ynoic acid;

5Z-11α,15S-dihydroxy-9a-deoxy-9a-methylene-2a,2b-dihomo-ω-pentanor-15-[(4'-vinyl)-cyclohexyl]-prostacycl-5-en-13-ynoic acid;

5Z-11α,15S-dihydroxy-9a-deoxy-9a-methylene-2a,2b-dihomo-ω-pentanor-15-[(4'-isopropylidene)-cyclopentyl]-prostacycl-5-en-13-ynoic acid;

5Z-11α,15S-dihydroxy-9a-deoxy-9a-methylene-2a,2b-dihomo-ω-pentanor-15-cyclopentyl-prostacycl-5-en-13-ynoic acid;

5Z-11α,15S-dihydroxy-9a-deoxy-9a-methylene-2a,2b-dihomo-ω-pentanor-15-[(3'-methyl)-cyclopentyl]-prostacycl-5-en-13-ynoic acid;

5Z-11α,15S-dihydroxy-9a-deoxy-9a-methylene-2a,2b-dihomo-ω-pentanor-15-[(3'-ethyl)-cyclopentyl]-prostacycl-5-en-13-ynoic acid;

5Z-11α,15S-dihydroxy-9a-deoxy-9a-methylene-2a,2b-dihomo-ω-pentanor-15-[(3'-isopropylidene)-cyclopentyl]-prostacycl-5-en-13-ynoic acid;

5Z-11α,15S-dihydroxy-9a-deoxy-9a-methylene-2a,2b-dihomo-ω-pentanor-15-cyclobutyl-prostacycl-5-en-13-ynoic acid, and the (+) enantiomers of all the hereabove listed compounds.

EXAMPLE 20

Using the esterification procedures described in the examples 14, 15, 16, 17 and 18 the methyl esters, β-piperidino ethyl ester and β-morpholino ethyl esters of the compounds obtained in the example 19 were prepared, in particular:

5E-11α,15S-dihydroxy-9a-deoxy-9a-methylene-2-nor-ω-pentanor-15-cyclohexyl-prostacycl-5-en-13-ynoic acid methyl ester;

5Z-11α,15S-dihydroxy-9a-deoxy-9a-methylene-2-nor-ω-pentanor-15-cyclohexyl-prostacycl-5-en-13-ynoic acid methyl ester;

5E-11α,15S-dihydroxy-9a-deoxy-9a-methylene-2a-homo-ω-pentanor-15-cyclohexyl-prostacycl-5-en-13-ynoic acid methyl ester;

5Z-11α,15S-dihydroxy-9a-deoxy-9a-methylene-2a-homo-ω-pentanor-15-cyclohexyl-prostacycl-5-en-13-ynoic acid methyl ester;

5E-11α,15S-dihydroxy-9a-deoxy-9a-methylene-2a,2b-dihomo-ω-pentanor-15-cyclohexyl-prostacycl-5-en-13-ynoic acid methyl ester;

5Z-11α,15S-dihydroxy-9a-deoxy-9a-methylene-2a,2b-dihomo-ω-pentanor-15-cyclohexyl-prostacycl-5-en-13-ynoic acid methyl ester;

5E-11α,15S-dihydroxy-9a-deoxy-9a-methylene-2-nor-ω-pentanor-15-cyclohexyl-prostacycl-5-en-13-ynoic acid β-piperidino ethyl ester;

5Z-11α, 15S-dihydroxy-9a-deoxy-9a-methylene-2-nor-ω-pentanor-15-cyclohexyl-prostacycl-5-en-13-ynoic acid β-piperidino ethyl ester;

5E-11α, 15S-dihydroxy-9a-deoxy-9a-methylene-2a-homo-ω-pentanor-15-cyclohexyl-prostacycl-5-en-13-ynoic acid β-piperidino ethyl ester;

5Z-11α, 15S-dihydroxy-9a-deoxy-9a-methylene-2a-homo-ω-pentanor-15-cyclohexyl-prostacycl-5-en-13-ynoic acid β-piperidino ethyl ester;

5E-11α, 15S-dihydroxy-9a-deoxy-9a-methylene-2a,2b-dihomo-ω-pentanor-15-cyclohexyl-prostacycl-5-en-13-ynoic acid β-piperidino ethyl ester;

5Z-11α, 15S-dihydroxy-9a-deoxy-9a-methylene-2a,2b-dihomo-ω-pentanor-15-cyclohexyl-prostacycl-5-en-13ynoic acid β-piperidino ethyl ester;

5E-11α, 15S-dihydroxy-9a-deoxy-9a-methylene-2-nor-ω- pentanor-15-cyclohexyl-prostacycl-5-en-13-ynoic acid β-morpholino ethyl ester;

5Z-11α, 15S-dihydroxy-9-deoxy-9a-methylene-2-nor-ω-pentanor-15-cyclohexyl-prostacycl-5-en-13-ynoic acid -β-morpholino ethyl ester;

5E-11α, 15S-dihydroxy-9a-deoxy-9a-methylene-2a-homo-ω-pentanor-15-cyclohexyl-prostacycl-5-en-13-ynoic acid -β-morpholino ethyl ester;

5Z-11α, 15S-dihydroxy-9a-deoxy-9a-methylene-2a-homo-ω-pentanor-15-cyclohexyl-prostacycl-5-en-13-ynoic acid -62 -morpholino ethyl ester;

5E-11α, 15S-dihydroxy-9a-deoxy-9a-methylene-2a,2b-dihomo-ω-pentanor-15-cyclohexyl-prostacycl-5-en-13-ynoic acid β-morpholino ethyl ester;

5Z-11α, 15S-dihydroxy-9a-deoxy-9a-methylene-2a,2b-dihomo-ω-pentanor-15-cyclohexyl-prostacycl-5-en-13-ynoic acid -β-morpholino ethyl ester;

5E-11α, 15S-dihydroxy-9a-deoxy-9a-methylene-2-nor-ω-pentanor-15-cyclopentyl-prostacycl-5-en-13-ynoic acid methyl ester;

5Z-11α, 15S-dihydroxy-9a-deoxy-9a-methylene-2-nor-ω-pentanor-15-cyclopentyl-prostacycl-5-en-13-ynoic acid methyl ester;

5E-11α, 15S-dihydroxy-9a-deoxy-9a-methylene-2a-homo-ω-pentanor-15-cyclopentyl-prostacycl-5-en-13-ynoic acid methyl ester;

5Z-11α, 15S-dihydroxy-9a-deoxy-9a-methylene-2a-homo-ω-pentanor-15-cyclopentyl-prostacycl-5en-13-ynoic acid methyl ester;

5E-11α, 15S-dihydroxy-9a-deoxy-9a-methylene-2a,2b-dihomo-ω-pentanor-15-cyclopentyl-prostacycl-5-en-13ynoic acid methyl ester;

5Z-11α, 15S-dihydroxy-9a-methylene-2a,2b-dihomo-ω-pentanor-15-cyclopentyl-prostacycl-5-en-13-ynoic acid methyl ester;

5E-11α, 15-dihydroxy-9a-deoxy-9a-methylene-2-nor-ω-pentanor-15-cyclopentyl-prostacycl-5-en-13-ynoic acid β-piperidino ethyl ester;

5Z-11α, 15S-dihydroxy-9a-deoxy-9a-methylene-2-nor-ω-pentanor-15-cyclopentyl-prostacycl-5-en-13-ynoic acid β-piperidino ethyl ester;

5E-11α, 15S-dihydroxy-9a-deoxy-9a-methylene-2a-homo-ω-pentanor-15-cyclopentyl-prostacycl-5-en-13-ynoic acid β-piperidino ethyl ester;

5Z-11α, 15S-dihydroxy-9a-deoxy-9a-methylene-2a-homo-ω-pentanor-15-cyclopentyl-prostacycl-5-en-13-ynoic acid β-piperidino ethyl ester;

5E-11α, 15S-dihydroxy-9a-deoxy-9a-methylene-2a,2b-dihomo-ω-pentanor-15-cyclopentyl-prostacycl-5-en-13-ynoic acid β-piperidino ethyl ester;

5Z-11α, 15S-dihydroxy-9a-deoxy-9a-methylene-2a,2b-dihomo-ω-pentanor-15-cyclopentyl-prostacycl-5-en-13-ynoic acid β-piperidino ethyl ester;

5E-11α, 15S-dihydroxy-9a-deoxy-9a-methylene-2-nor-ω-pentanor-15-cyclopentyl-prostacycl-5-en-13-ynoic acid β-morpholino ethyl ester;

5Z-11α, 15S-dihydroxy-9a-deoxy-9a-methylene-2-nor-ω-pentanor-15-cyclopentyl-prostacycl-5-en-13-ynoic acid β-morpholino ethyl ester;

5E-11α, 15S-dihydroxy-9a-deoxy-9a-methylene-2a-homo-ω-pentanor-prostacycl-15-cyclopentyl-prostacycl-5-en-13-ynoic acid β-morpholino ethyl ester;

5Z-11α, 15S-dihydroxy-9a-deoxy-9a-methylene-2a-homo-ω-pentanor-15-cyclopentyl-prostacycl-5-en-13-ynoic acid β-morpholino ethyl ester;

5E-11α, 15S-dihydroxy-9a-deoxy-9a-methylene-2a,2b-dihomo-ω-pentanor-15-cyclopentyl-prostacycl-5-en-13ynoic acid β-morpholino ethyl ester;

5Z-11α, 15S-dihydroxy-9a-deoxy-9a-methylene-2a,2b-dihomo-ω-pentanor-15-cyclopentyl-prostacycl-5-en-13-ynoic acid β-morpholino ethyl ester;

and the (+) enantiomers of all the hereabove listed compounds.

EXAMPLE 21

Using in the procedure of the example 11 the bicyclo[3.3.0]octane-3'R-hydroxy derivatives obtained in the examples 9 and 10, the 15R-hydroxy epimers of all the compounds obtained in the examples 11 to 20 were prepared, in particular:

5E-11α, 15R-dihydroxy-9a-deoxy-9a-methylene-ω-pentanor-15-cyclohexyl-prostacycl-5-en-13-ynoic acid;

5E-11α, 15R-dihydroxy-9a-deoxy-9a-methylene-ω-pentanor-15-[(4'-methyl)-cyclohexyl]-prostacycl-5-en-13-ynoic acid;

5E-11α, 15R-dihydroxy-9a-deoxy-9a-methylene-ω-pentanor-15-[(4'-ethyl)-cyclohexyl]-prostacycl-5-en-13-ynoic acid;

5E-11α, 15R-dihydroxy-9a-deoxy-9a-methylene-ω-pentanor-15-[(4'-tert.butyl)-cyclohexyl]-prostacycl-5-en-13-ynoic acid;

5E-11α, 15R-dihydroxy-9a-deoxy-9a-methylene-ω-pentanor-15-[(4'-vinyl)-cyclohexyl])-prostacycl-5-en-13-ynoic acid;

5E-11α, 15R-dihydroxy-9a-deoxy-9a-methylene-ω-pentanor--15-[(4'-isopropylidene)-cyclohexyl]-prostacycl-5-en-13-ynoic acid;

5E-11α, 15R-dihydroxy-9a-deoxy-9a-methylene-ω-pentanor--15-cyclopentyl-prostacycl-5-en-13-ynoic acid;

5E-11α, 15R-dihydroxy-9a-deoxy-9a-methylene-ω-pentanor-15-[(3'-methyl)-cyclopentyl]-prostacycl-5-en-13-ynoic acid;

5E-11α, 15R-dihydroxy-9a-deoxy-9a-methylene-ω-pentanor-15-[(3'-ethyl)-cyclopentyl]-prostacycl-5-en-13-ynoic acid;

5-11α, 15R-dihydroxy-9a-deoxy-9a-methylene-ω-pentanor-15-[(3'-isopropylidene)-cyclopentyl]-prostacycl-5-en-13-ynoic acid;

5E-11α, 15R-dihydroxy-9a-deoxy-9a-methylene-ω-pentanor-15-cyclobutyl-prostacycl-5-en-13-ynoic acid;

5E-11α, 15R-dihydroxy-9a-deoxy-9a-methylene-ω-pentanor-15-cyclohexyl-prostacycl-5-en-13-ynoic acid;

5Z-11α, 15R-dihydroxy-9a-deoxy-9a-methylene-ω-pentanor-15-[(4'-methyl)-cyclohexyl]-prostacycl-5-en-13-ynoic acid;

5Z-11α, 15R-dihydroxy-9a-deoxy-9a-methylene-107-pentanor-15-[(-4′ethyl)-cyclohexyl]-prostacycl-5-en 13-ynoic acid;

5Z-11α, 15R-dihydroxy-9a-deoxy-9a-methylene-ω-pentanor-15-[(4′-tert.butyl)-cyclohexyl]-prostacycl-5-en-13-ynoic acid;

5Z-11α, 15R-dihydroxy-9a-deoxy-9a-methylene-ω-pentanor-15-[(4′-vinyl)-cyclohexyl]-prostacycl-5-en-13-ynoic acid;

5Z-11α, 15R-dihydroxy-9a-deoxy-9a-methylene-ω-pentanor-15-[(4′-isopropylidene)-cyclohexyl]-prostacycl-5-en-13-ynoic acid;

5Z-11α, 15R-dihydroxy-9a-deoxy-9a-methylene-ω-pentanor-15-cyclopentyl-prostacycl-5-en-13-ynoic acid;

5Z-11α, 15R-dihydroxy-9a-deoxy-9a-methylene-ω-pentanor-15-[(3′-methyl)-cyclopentyl]-prostacycl-5-en-13-ynoic acid;

5Z-11α, 15R-dihydroxy-9a-deoxy-9a-methylene-ω-pentanor-15-[(3′-ethyl)-cyclopentyl]-prostacycl-5-en-13-ynoic acid;

5Z-11α, 15R-dihydroxy-9a-deoxy-9a-methylene-ω-pentanor-15-[(3′-isopropylidene)-cyclopentyl]-prostacycl-5-en-13-ynoic acid;

5Z-11α, 15R-dihydroxy-9a-deoxy-9a-methylene-ω-pentanor-15-cyclobutyl-prostacycl-5-en-13-ynoic acid;

5Z-11α, 15R-dihydroxy-9a-deoxy-9a-methylene-ω-pentanor-15-cyclohexyl-prostacycl-5-en-13-ynoic acid;

5(Z,E)-11α, 15R-dihydroxy-9a-deoxy-9a-methylene-ω-pentanor-15-[(4′-methyl)-cyclohexyl]-prostacycl-5-en-13-ynoic acid;

5(Z,E)-11α, 15R-dihydroxy-9a-deoxy-9a-methylene-ω-pentanor-15-[(4′-ethyl)-cyclohexyl]-prostacycl-5-en-13-ynoic acid;

5(Z,E)-11α, 15R-dihydroxy-9a-deoxy-9a-methylene-ω-pentanor-15-[(4′-tert.butyl)-cyclohexyl]-prostacycl-5-en-13-ynoic acid;

5(Z,E)-11α, 15R-dihydroxy-9a-deoxy-9a-methylene-ω-pentanor-15-[(4′-vinyl)-cyclohexyl]-prostacycl-5-en-13-ynoic acid;

5(Z,E)-11α, 15R-dihydroxy-9a-deoxy-9a-methylene-ω-pentanor-15-[(4′-isopropylidene)-cyclohexyl]-prostacycl-5-en-13-ynoic acid;

5(Z,E)-11α, 15R-dihydroxy-9a-deoxy-9a-methylene-ω-pentanor-15-cyclopentyl-prostacycl-5-en-13-ynoic acid;

5(Z,E)-11α, 15R-dihydroxy-9a-deoxy-9a-methylene-ω-pentanor-15-[(3′-methyl)-cyclopentyl]-prostacycl-5-en-13-ynoic acid;

5(Z,E)-11α, 15R-dihydroxy-9a-deoxy-9a-methylene-ω-pentanor-15-[(3′-ethyl)-cyclopentyl]-prostacycl-5-en-13-ynoic acid;

5(Z,E)-11α, 15R-dihydroxy-9a-deoxy-9a-methylene-ω-pentanor-15-[(3′-isopropylidene)-cyclopentyl]-prostacycl-5-en-13-ynoic acid;

5(Z,E)-11α, 15R-dihydroxy-9a-deoxy-9a-methylene-ω-pentanor-15-cyclobutyl-prostacycl-5-en-13-ynoic acid;

and the (+) enantiomers of the hereabove listed compounds.

EXAMPLE 22

Using the esterification procedure described in the example 14 the methyl esters of the compounds obtained in the example 21 were prepared, in particular:

5E-11α,15R-dihydroxy-9a-deoxy-9a-methylene-ω-pentanor-15-cyclohexyl-prostacycl-5-en-13-ynoic acid methyl ester;

5E-11α, 15R-dihydroxy-9a-deoxy-9a-methylene-ω-pentanor-15-[(4′--methyl)-cyclohexyl]-prostacycl-5-en-13-ynoic acid methyl ester;

5E-11α, 15R-dihydroxy-9a-deoxy-9a-methylene-107-pentanor-15[(4′-ethyl)-cyclohexyl]-prostacycl-5-en-13-ynoic acid methyl ester;

5E-11α, 15R-dihydroxy-9a-deoxy-9a-methylene-ω-pentanor-15-[(4′-tert.butyl)-cyclohexyl]-prostacycl-5-en-13-ynoic acid methyl ester;

-5E-11α,15R-dihydroxy-9a-deoxy-9a-methylene-ω-pentanor-15-(4′-vinyl)cyclohexyl]-prostacycl-5-en-13-ynoic acid methyl ester;

5E-11α, 15R-dihydroxy-9a-deoxy-9a-methylene-ω-pentanor-15-[(4′-isopropylidene)-cyclohexyl]prostacycl-5-en-13-ynoic acid methyl ester;

5E-11α, 15R-dihydroxy-9a-deoxy-9a-methylene-ω-pentanor-15-cyclopentyl-prostacycl-5-en-13-ynoic acid methyl ester;

5E-11α, 15R-dihydroxy-9a-deoxy-9a-methylene-ω-pentanor-15-[(3′-methyl)-cyclopentyl]-prostacycl-5-en-13-ynoic acid methyl ester;

5E-11α, 15R-dihydroxy-9a-deoxy-9a-methylene-ω-pentanor-15-[(3′-ethyl)-cyclopentyl]-prostacycl-5-en-13-ynoic acid methyl ester;

5E-11α, 15R-dihydroxy-9a-deoxy-9a-methylene-ω-pentanor-15-[(3′-tert.butyl)-cyclopentyl]-prostacycl-5-en-13-ynoic acid methyl ester;

5E-11α, 15R-dihydroxy-9a-deoxy-]a-methylene-ω-pentanor-15-[(3′-vinyl)-cyclopentyl]-prostacycl-5-en-13-ynoic acid methyl ester;

5E-11α, 15R-dihydroxy-9a-deoxy-9a-methylene-ω-pentanor-15-[(3′-isopropylidene cyclopentyl])-prostacycl-5-en-13ynoic acid methyl ester;

5E-11α, 15R-dihydroxy-9a-deoxy-9a-methylene-ω-pentanor-15-cyclobutyl-prostacycl-5-en-13-ynoic acid methyl ester, and the (+) enantiomers of the above listed compounds.

EXAMPLE 23

A solution of (+) 5E-11α, 15S-dihydroxy-9a-deoxy-9a-methylene-ωpentanor-15-cyclopentyl-prostacycl-5-en-13-ynoic acid (0.60 g) in 5 ml of ethanol was treated with a stoichiometric amount of 01 N NaOH aqueous solution. The alcohol was removed in vacuo and the aqueous solution was lyophilized to give 0.62 g of dry (+)5E-11α, 15S-dihydroxy-9a-deoxy-9a-methylene-ω-pentanor-15-cyclopentyl-prostacycl-5-en-13-ynoic acid sodium salt.

EXAMPLE 24

A solution of (+)5E-11α, 15S-dihydroxy-9a-deoxy-9a-methylene-ω-pentanor-15-cyclopentyl-prostacycl-5-en-13ynoic acid (500 μg) in ethanol (6 ml) was sterilized by passage through a bacteria-retaining filter. Portions of 0.1 ml were placed into 1 ml ampoules which were then sealed. The content of an ampoule was diluted with 1 ml of tris-HCl buffer solution having pH 8.6 to give a solution ready for administration by injection.

We claim:

1. An optionally active or racemic compound of the following formula (I)

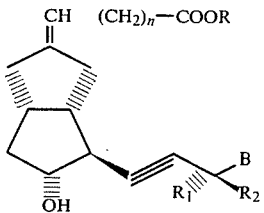

(I)

wherein

R is hydrogen or a $C_1$-$C_6$ alkyl group optionally substituted by a group

wherein each of $R_3$ and $R_4$ is, independently, hydrogen or $C_1$-$C_6$ alkyl, or $R_3$ and $R_4$, taken together with the nitrogen atom to which they are linked, form a pentatomic or hexatomic heteromonocyclic ring optionally containing a further heteroatom chosen from O and S;

n is an integer of 1 to 5 one of $R_1$ and $R_2$ is hydrogen or $C_1$-$C_6$ alkyl and the other is hydroxy; and B represents: (a) a $C_4$-$C_7$ monocycloaliphatic group either unsubstituted or substituted by one or more substituents chosen from $C_1$-$C_6$ alkyl, $C_2$-$C_6$ alkylidene; (b) norbornyl; or (c) adamantyl, and the pharmaceutically or veterinarily acceptable salts thereof.

2. An optically active or racemic compound having the formula (I) reported above in claim 1 wherein: R is hydrogen, $C_1$-$C_6$ alkyl, βpiperidino-$C_1$-$C_3$ alkyl or β-morpholino-$C_2$-$C_3$ alkyl; n is 3 or 4; one of $R_1$ and $R_2$ is hydrogen and the other is hydroxy; and B is cyclopentyl or cyclohexyl, either unsubstituted or substituted by a substituent chosen from $C_1$-$C_4$ alkyl, $C_2$-$C_4$ alkenyl and $C_1$-$C_4$ alkylidene, and the pharmaceutically or veterinarily acceptable salts thereof.

3. An optically active or recemic compound according to claim 2 wherein B is cyclopentyl.

4. A compound, either racemate or (+) anantiomer, chosen from the group consisting of:

5E-11α15S-dihydroxy-9a-deoxy-9a-methylene-107 -pentanor-15-[(3'-methyl)-cyclopentyl]-prostacycl-5-en-13-ynoic acid;

5E-11α,15S-hydroxy-9a-deoxy-9-methylene-ω-pentanor-15-[(3'-ethyl)-cyclopentyl]prostacycl-5-en-13-ynoic acid; acid;

5E-11α, 15S-dihydroxy-9a-deoxy-9a-methylene-ω-pentanor-15-[(3'-isopropylidene)-cyclopentyl]prostacycl-5-en-13-ynoic acid;

5E-11α, 15S-dihydroxy-9a-deoxy-9a-methylene-ω-pentanor-15-cyclohexyl-prostacyclo-5-en-13-ynoic acid;

5E-11α, 15S-dihydroxyl-9a-deoxy-9a-methylene-ω-pentanor-15-[(4'-methyl)-cyclohexyl]-prostacycl-5-en-13-ynoic acid;

5E-11α, 15S-dihydroxy-9a-deoxy-9a-methylene-ω-pentanor-15-[(4'-ethyl)-cyclohexyl]-prostacycl-5-en-13-ynoic acid;

5E-11α, 15S-dihydroxy-9a-deoxy-9a-methylene-ω-pentanor-15-[(4'-isopropylidene)-cyclohexyl]-prostacycl-5-en-13-ynoic acid;

and the pharmaceutically or veterinarily acceptable salts thereof and the $C_1$-$C_6$ alkyl-esters, β-piperidinoethyl and 62 -morpholinoethyl esters thereof.

5. A compound, either racemate or (+) enantiomer, chosen from the group consisting of:

5Z-11α, 15S-dihydroxy-9a-deoxy-9a-methylene-ω-pentanor-15-cyclopentyl-prostacycl-5-en-13ynoic aicd;

5Z-11α, 15S-dihydroxy-9a-deoxy-9a-methylene-ω-pentanor-15-[(3'-methyl)-cyclopentyl]-prostacycl-5-en-13ynoic acid;

5Z-11α, 15S-dihydroxy-9a-deoxy-9a-methylene-ω-pentanor-15-[(3'-ethyl)-cyclopentyl]-prostacycl-5-en-13ynoic acid;

5Z-11α, 15S-dihydroxy-9a-deoxy-9a-methylene-ω-pentanor-15-[(3'-isopropylidene)-cyclopentyl]-prostacycl-5-en-13ynoic acid 5Z-11α, 15S-dihydroxy-9a-deoxy-9a-methylene-ω-pentanor-15-cyclohexyl-prostacycl-5-en-13ynoic acid;

5Z-11α, 15S-dihydroxy-9a-deoxy-9a-methylene-ω-pentanor-15-](4'-methyl)-cyclohexyl]-prostacycl-5-en 13ynoic acid;

5Z-11α, 15S-dihydroxy-9a-deoxy-9a-methylene-ω-pentanor-15-[(4'-ethyl)-cyclohexyl]-prostacycl-5-en-13ynoic acid;

5Z-11α, 15S-dihydroxy-9a-deoxy-9a-methylene-ω-pentanor-15-[(4'-isopropylidene)-cyclohexyl]-prostacycl-5-en-13ynoic acid;

and the pharmaceutically or veterinarily acceptable salts thereof and the $C_1$-$C_6$ alkyl-esters, β-piperdinoethyl and β-morpholinoethyl esters thereof.

6. A compound, either racemate or (+) enantiomer, chosen from the group consisting of:

5(Z,E)-11α, 15S-dihydroxy-9a-deoxy-9a-methylene-ω-pentanor-15-cyclopentyl-prostacycl-5-en-13-ynoic acid;

5(Z,E)-11α, 15S-dihydroxy-9a-deoxy-9a-methylene-ω-pentanor-15-[(3'-methyl)-cyclopentyl]-prostacycl-5-en-13-ynoic acid;

5(Z,E)-11α, 15S-dihydroxy-9a-deoxy-9a-methylene-ω-pentanor-15-[(3'-ethyl)-cyclopentyl]-prostacycl-5-en-13-ynoic acid;

5(Z,E)-11α, 15S-dihydroxy-9a-deoxy-9a-methylene-ω-pentanor-15-[(3'-isopropylidene)-cyclopentyl]-prostacycl-5-en-13-ynoic acid;

5(Z,E)-11α, 15S-dihydroxy-9a-deoxy-9a-methylene-ω-pentanor-15-cyclohexyl-prostacycl-5-en-13-ynoic acid;

5(Z,E)-11α, 15S-dihydroxy-9a-deoxy-9a-methylene-ω-pentanor-15-[(4'-methyl)-cyclohexyl]-prostacycl-5-en-13-ynoic acid;

5(Z,E)-11α, 15S-dihydroxy-9a-deoxy-9a-methylene-ω-pentanor-15-[(4'-ethyl)-cyclohexyl]-prostacycl-5-en-13-ynoic acid;

5(Z,E)-11α, 15S-dihydroxy-9a-deoxy-9a-methylene-ω-pentanor-15-[(4'-isopropylidene)-cyclohexyl]-prostacycl-5-en-13-ynoic acid;

and the pharmaceutically or veterinarily acceptable salts thereof and the $C_1$-$C_6$ alkyl-esters, β-piperidinoethyl-esters and β-morpholinoethyl-esters thereof.

7. The compound 5E-11α, 15S-dihydroxy-9a-deoxy-9a-methylene-ω-pentanor-15-cyclopentyl-prostacycl-5-en-13-ynoic acid, either racemate or (+) enantiomer, and the pharmaceutically or veterinarily acceptable salts thereof and the $C_1$-$C_6$ alkyl esters, β-piperidinoethyl esters and β-morpholinoethyl esters thereof.

8. A $C_1$-$C_6$ alkyl ester according to claim 8 wherein the ester is the methyl ester.

9. A $C_1$–$C_6$ alkyl ester according to claim 8 wherein the ester is the methyl ester.

10. The β-piperidino-ethyl ester of the compound of claim 7.

11. The β-morpholino-ethyl ester of the compound of claim 7.

12. A method of inhibiting blood platelet aggregation in a patient in need of it, said method comprising administering an effective amount of a compound of claim 1.

13. A method of inhibiting blood platelet aggregation in a patient in need of it, said method comprising administering an effective amount of a pharmaceutical composition of claim 12.

14. A pharmaceutical or veterinary composition useful for inhibition of platelet aggregation, said composition comprising a therapeutically effective amount of a compound of formula (I) or a pharmaceutically or veterinally acceptable salt thereof as claimed in claim 1, in association with a suitable carrier and/or diluent.

* * * * *

UNITED STATES PATENT AND TRADEMARK OFFICE
CERTIFICATE OF CORRECTION

PATENT NO. : 4,514,396
DATED : April 30, 1985
INVENTOR(S) : MONGELLI et al

It is certified that error appears in the above-identified patent and that said Letters Patent is hereby corrected as shown below:

Column 1 last line delete "contemlated" and replace by
--contemplated--
Column 2 line 20 in the upper part of formula (I) insert the wavy line --∼-- between CH and $(CH_2)_n$
Column 2 last line insert the symbol of the wedged line --◄-- into the brackets;
Column 3 line 26 delete "formual(I)" and replace by --formula(I)--
Column 5 line 54 delete "formula(1)" and replace by --formula(I)--
Column 5 line 63 delete "enanitomers:" and replace by --enantiomers:--
Column 6 line 28 delete "[(30'-" and replace by --[(3'- --
Column 7 line 5 delete formula(11) and replace by --formula(II)--
Column 7 line 21 delete formula(111) and replace by --formula(III)--
Column 7 lines 58 and 59 delete "preferbly" and replace by --preferably--
Column 8 line 64 delete "esterfication" and replace by --esterification--
Column 8 line 65 delete "diazolkane" and replace by --diazoalkane--
Column 9 line 20 delete "methylane chloride" and replace by --methylene chloride--
Column 9 line 23 delete "optical" and replace by --optional--
Column 9 line 65 delete "formula(11) and replace by --formula(II)--
Column 10 line 5 insert the dotted line in the left side of the formula (IV)

UNITED STATES PATENT AND TRADEMARK OFFICE
CERTIFICATE OF CORRECTION

PATENT NO. : 4,514,396

DATED : April 30, 1985

INVENTOR(S) : MONGELLI et al

It is certified that error appears in the above-identified patent and that said Letters Patent is hereby corrected as shown below:

Column 27 line 15 delete "washsed" and replace by --washed--
Column 31 line 27 delete "etster" and replace by --ester--
Column 33 line 3 delete "-62-morpholino-" and replace by
-- -$\beta$-morpholino- --
Column 33 line 9 delete "-$\beta$-morpholic-" and replace by
-- -$\beta$-morpholino- --
Column 37 line 27 delete "-62-morpholino-" and replace by
-- -$\beta$-morpholino- --
Column 40 line 67 delete "optionally" and replace by --optically--
Column 41 line 2 in the upper part of the formula insert the wavy line($\sim$) between CH and $(CH_2)_n$.
Column 41 line 32 delete "substituents chosen from $C_1$-$C_6$ alky-" and replace by --substituents chosen from $C_1$-$C_6$ alkyl, $C_1$-$C_6$ alky- --
Column 41 line 4 of claim 2 delete " $\beta$-morpholino-$C_2$-$C_3$ alkyl;.." and replace by -- $\beta$-morpholino-$C_1$ - $C_3$ alkyl;--
Column 41 line 3 of claim 4 delete "-107" and replace by -- -w"--;
Column 41 line 45 delete "recemic" and replace by --racemic--
Column 41 line 54 delete "acid;"
Column 42 line 3 delete "62-morpholinoethyl" and replace by
-- $\beta$-morpholino-ethyl--

UNITED STATES PATENT AND TRADEMARK OFFICE
CERTIFICATE OF CORRECTION

PATENT NO. : 4,514,396

DATED : April 30, 1985

INVENTOR(S) : MONGELLI et al

It is certified that error appears in the above-identified patent and that said Letters Patent is hereby corrected as shown below:

Column 42 lines 66 and 67 delete "and the $C_1 - C_6$ alkyl esters, $\beta$-piperidino-ethyl esters and $\beta$-morpholinoethyl esters thereof"
Column 42 claim 8 lines 1 and 2 delete "A $C_1-C_6$ alkyl ester according to claim 8 wherein the ester is the methyl ester."
and replace by --A $C_1-C_6$ alkyl ester of the compound of claim 7.--
Columns 43 and 44 re-number claim 12 as claim 13, re-number claim 13 as claim 14 and re-number claim 14 as claim 12.

Signed and Sealed this

Third Day of December 1985

[SEAL]

Attest:

Attesting Officer

DONALD J. QUIGG

Commissioner of Patents and Trademarks